United States Patent
Kohno et al.

(10) Patent No.: US 8,232,319 B2
(45) Date of Patent: Jul. 31, 2012

(54) AMINO PHOSPHATE DERIVATIVE AND S1P RECEPTOR MODULATOR HAVING SAME AS AN ACTIVE INGREDIENT

(75) Inventors: Yasushi Kohno, Tochigi (JP); Kiyoshi Fujii, Tochigi (JP); Tatsuhiro Saito, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 612 days.

(21) Appl. No.: 12/310,007

(22) PCT Filed: Aug. 7, 2007

(86) PCT No.: PCT/JP2007/065397
§ 371 (c)(1),
(2), (4) Date: Jun. 1, 2009

(87) PCT Pub. No.: WO2008/018427
PCT Pub. Date: Feb. 14, 2008

(65) Prior Publication Data
US 2009/0325907 A1    Dec. 31, 2009

(30) Foreign Application Priority Data
Aug. 8, 2006  (JP) ................. 2006-215280

(51) Int. Cl.
*A61K 31/185* (2006.01)
*C07F 9/28* (2006.01)
(52) U.S. Cl. .......................... 514/576; 564/15
(58) Field of Classification Search ........... 564/15; 514/576
See application file for complete search history.

(56) References Cited

U.S. PATENT DOCUMENTS

| | | | |
|---|---|---|---|
| 5,447,922 A | 9/1995 | Lawrence et al. | |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,960,692 B2 | 11/2005 | Kohno et al. | |
| 6,963,012 B2 | 11/2005 | Kohno et al. | |
| 7,456,157 B2 | 11/2008 | Kohno et al. | |
| 7,482,491 B2 | 1/2009 | Kohno et al. | |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147490 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |
| 2005/0222422 A1 | 10/2005 | Lynch et al. | |
| 2005/0245575 A1 | 11/2005 | Chen et al. | |
| 2006/0046979 A1 | 3/2006 | Foster et al. | |
| 2006/0089334 A1 | 4/2006 | Budhu et al. | |
| 2006/0135622 A1 | 6/2006 | Kohno et al. | |
| 2006/0135786 A1 | 6/2006 | Saha et al. | |
| 2006/0148830 A1 | 7/2006 | Terakado et al. | |
| 2006/0148844 A1 | 7/2006 | Nakade et al. | |
| 2006/0160771 A1 | 7/2006 | Kohno et al. | |
| 2006/0161005 A1 | 7/2006 | Doherty et al. | |
| 2006/0166940 A1 | 7/2006 | Buehlmayer et al. | |
| 2006/0211656 A1 | 9/2006 | Albert et al. | |
| 2006/0211658 A1 | 9/2006 | Hinterding et al. | |
| 2006/0252741 A1 | 11/2006 | Colandrea et al. | |

(Continued)

FOREIGN PATENT DOCUMENTS

JP     2002-53575     2/2002

(Continued)

OTHER PUBLICATIONS

Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.

(Continued)

*Primary Examiner* — Peter G O'Sullivan
(74) *Attorney, Agent, or Firm* — Wenderoth, Lind & Ponack, L.L.P.

(57) ABSTRACT

To provide an amino phosphate derivative having an excellent sphingosine-1-phosphate (S1P) receptor modulatory action. As a result of continued intensive research to create a highly safe compound which has an S1P receptor modulatory action, is has been discovered that an amino phosphate derivative represented by the following general formula (1),

[Chemical formula 1]

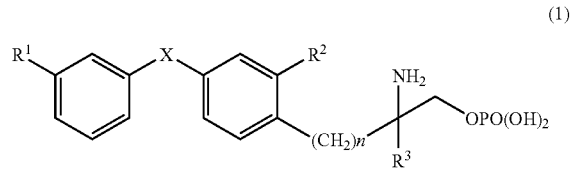

(1)

has a strong S1P receptor modulatory action.

18 Claims, No Drawings

U.S. PATENT DOCUMENTS

| | | | |
|---|---|---|---|
| 2006/0264403 A1 | 11/2006 | Albert | |
| 2007/0010494 A1 | 1/2007 | Ehrhardt et al. | |
| 2007/0043014 A1 | 2/2007 | Doherty et al. | |
| 2007/0088002 A1 | 4/2007 | Lynch et al. | |
| 2007/0135501 A1 | 6/2007 | Hinterding et al. | |
| 2007/0149597 A1 | 6/2007 | Nishi et al. | |
| 2007/0167410 A1 | 7/2007 | Pan et al. | |
| 2007/0167425 A1 | 7/2007 | Nakade et al. | |
| 2007/0191468 A1 | 8/2007 | Nishi et al. | |
| 2007/0203100 A1 | 8/2007 | Pan et al. | |
| 2007/0225260 A1 | 9/2007 | Hinterding et al. | |
| 2008/0025973 A1 | 1/2008 | Fleenor et al. | |
| 2008/0027508 A1 | 1/2008 | Chu | |
| 2008/0032923 A1 | 2/2008 | Kudou et al. | |
| 2008/0153882 A1 | 6/2008 | Nishi et al. | |
| 2008/0161410 A1 | 7/2008 | Kusters et al. | |
| 2008/0200438 A1 | 8/2008 | Albert et al. | |
| 2008/0207584 A1 | 8/2008 | Habashita et al. | |
| 2008/0207941 A1 | 8/2008 | Tsubuki et al. | |
| 2008/0249093 A1 | 10/2008 | Colandrea et al. | |
| 2009/0023797 A1 | 1/2009 | Azzaoui et al. | |

FOREIGN PATENT DOCUMENTS

| | | |
|---|---|---|
| JP | 2002-316985 | 10/2002 |
| JP | 2003-137894 | 5/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-47899 | 2/2005 |
| JP | 2005-247691 | 9/2005 |
| WO | 01/98301 | 12/2001 |
| WO | 03/040097 | 5/2003 |
| WO | 03/051876 | 6/2003 |
| WO | 2004/074297 | 9/2004 |
| WO | 2005/014525 | 2/2005 |
| WO | 2005/014603 | 2/2005 |
| WO | 2005/063671 | 7/2005 |
| WO | 2006/041015 | 4/2006 |
| WO | 2006/063033 | 6/2006 |
| WO | 2006/129688 | 12/2006 |
| WO | 2007/043433 | 4/2007 |
| WO | 2007/043568 | 4/2007 |
| WO | 2007/091501 | 8/2007 |
| WO | 2007/126042 | 11/2007 |

OTHER PUBLICATIONS

Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.
Yasuyuki Igarashi, Sphingosine-1-Phosphate as an Intercellular Signaling Molecule, Ann. NY Acad. Sci., 1998, vol. 845, pp. 19-31.
Jacobs et al., Intramuscular Interferon Beta-1a for Disease Progression in Relapsing Multiple Sclerosis, Ann. Neurol., 1996, vol. 39, No. 3, pp. 285-294.
Weinshenker et al., A Randomized Trial of Plasma Exchange in Acute Central Nervous System Inflammatory Demyelinating Disease, Ann. Neurol., 1999, vol. 46, No. 6, pp. 878-886.
Ganem et al., The Molecular Biology of the Hepatitis B Virus, Annu. Rev. Biochem., 1987, vol. 56 pp. 651-693.
Kaneko et al., Sphingosine-1-phosphate receptor agonists suppress concanavalin A-induced hepatic injury in mice, Biochem. and Biophys. Res. Commun., 2006, vol. 345, pp. 85-92.
Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.
Klein et al., Total Synthesis and Antifungal Evaluation of Cyclic Aminohexapeptides, Bioorg. Med. Chem., 2000, vol. 8, pp. 167-1696.
Hashimoto et al., β-Phenylselenoalanine as a dehydroalanine precursor-efficient synthesis of alternariolide (AM-toxin I), Chem. Commun., 1996, pp. 1139-1140.

Levkau et al., High-Density Lipoprotein Stimulates Myocardial Perfusion in Vivo, Circulation, 2004, vol. 110, pp. 3355-3359.
Salomone et al., $S1P_3$ receptors mediate the potent constriction of cerebral arteries by sphingosine-1-phosphate, Eur. J. Pharmacol., 2003, vol. 469, pp. 125-134.
Heneghan et al., Current and Novel Immunosuppressive Therapy for Autoimmune Hepatitis, Hepatology, 2002, vol. 35, No. 1, pp. 7-13.
Francis V. Chisari, Cytotoxic T Cells and Viral Hepatitis, J. Clin. Invest., Apr. 1997, vol. 99, No. 7, pp. 1472-1477.
Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.
Brinkmann et al., The Immune Modulator FTY720 Targets Sphingosine 1-Phosphate Receptors, J. Biol. Chem., 2002, vol. 277, No. 24, pp. 21453-21457.
Sanna et al., Sphingosine 1-Phosphate (S1P) Receptor Subtypes $S1P_1$ and $S1P_3$, Respectively, Regulate Lymphocyte Recirculation and Heart Rate, J. Biol. Chem., Apr. 2, 2004, vol. 279, No. 14, pp. 13839-13848.
Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.
George C. Ebers, Randomised double-blind placebo-controlled study of interferon β-1a in relapsing/remitting multiple sclerosis, Lancet, Nov. 7, 1998, vol. 352, pp. 1498-1501.
Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.
Fried et al., Peginterferon Alfa-2a Plus Ribavirin for Chronic Hepatitis C Virus Infection, N. Engl. J. Med., Sep. 26, 2002, vol. 347, No. 13, pp. 975-982.
Mailliard et al., Suppressing Hepatitis B without Resistance—So Far, So Good, N. Engl. J. Med., Feb. 27, 2003, vol. 348, No. 9, pp. 848-850.
Niessen et al., Dentritic cell PAR1-S1P3 signalling couples coagulation and inflammation, Nature, Apr. 3, 2008, vol. 452, No. 3, pp. 654-658.
IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.
Paty et al., Interferon beta-1b is effective in relapsing-remitting multiple sclerosis. II MRI analysis results of a multicenter, randomized, double-blind, placebo-controlled trial, Neurology, Apr. 1993, vol. 43, pp. 662-667.
Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.
Zivadinov et al., Effects of IV methylprednisolone on brain atrophy in relapsing-remitting MS, Neurology, 2001, vol. 57, pp. 1239-1247.
Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.
Rudick et al., Management of Multiple Cclerosis, N. Engl. J. Med., Nov. 27, 1997, vol. 337, No. 22, pp. 1604-1611.
Daniel K. Podolsky, Inflammatory Bowel Disease, N. Engl. J. Med., Aug. 8, 2002, vol. 347, No. 6, pp. 417-429.
Kappos et al., Oral Fingolimod (FTY720) for Relapsing Multiple Sclerosis, N. Engl. J. Med., Sep. 14, 2006, vol. 355, No. 11, pp. 1124-1140.
Viscido et al., Inflammatory bowel diseases: clinical update of practical guidelines, Nucl. Med. Commun., 2005, vol. 26, No. 7, pp. 649-655.
Gon et al., $S1P_3$ receptor-induced reorganization of epithelial tight junctions comprises lung barrier integrity and is potentiated by TNF, PNAS, Jun. 28, 2005, vol. 102, No. 26, pp. 9270-9275.
Saito et al., Hepatitis C virus infection is associated with the development of hepatocellular carcinoma, Proc. Natl. Acad. Sci. USA, Sep. 1990, vol. 87, pp. 6547-6549.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrohedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

English translation of Office Action issued Oct. 21, 2010 in Russian Application corresponding to U.S. Appl. No. 12/083,224.

Julien Davaille et al., "Sphingosine 1-Phosphate Triggers Both Apoptotic and Survival Signals for Human Hepatic Myofibroblasts", J. Biol. Chem., vol. 277, No. 40, pp. 37323-37330 (2002).

International Search Report dated Oct. 2, 2007 in the International (PCT) Application PCT/JP2007/065397 of which the present application is the U.S. National Stage.

AMINO PHOSPHATE DERIVATIVE AND S1P RECEPTOR MODULATOR HAVING SAME AS AN ACTIVE INGREDIENT

TECHNICAL FIELD

The present invention relates to a highly safe amino phosphate derivative useful as an S1P (sphingosine-1-phosphate) receptor modulator, and a salt and a hydrate thereof.

BACKGROUND ART

Although it was considered that sphingosine-1-phosphate (S1P) was only an intermediate metabolite in sphingosine metabolism, it has been reported that S1P has a cell growth stimulatory activity and a control action of cell movement function. Thus, it is becoming clear that S1P is a new lipid mediator which demonstrates a variety of physiological functions, such as an apoptotic activity, cell morphology regulatory action, and vasoconstriction (Non-patent Documents 1 and 2). Although this lipid has two actions, as an intracellular second messenger and as an intercellular mediator, research concerning its action as an intercellular mediator is especially active. It has been reported that signaling is carried out via a plurality of G protein-conjugated receptors (Endothelial Differentiation Gene, EDG) which are present on the cell membrane surface (Non-patent Documents 1 and 3). Currently, five S1P receptor subtypes are known, Edg-1, Edg-3, Edg-5, Edg-6, and Edg-8, which are respectively referred to as $S1P_1$, $S1P_3$, $S1P_2$, $S1P_4$, and $S1P_5$.

From the various research concerning these S1P receptors, it has been reported that a so-called S1P receptor modulator, which exhibits an agonistic activity or an antagonistic activity against such receptors, demonstrates effectiveness against a wide variety of diseases. For example, it has been disclosed that a compound which acts on Edg-5 ($S1P_2$) is effective against arteriosclerosis, renal fibrosis, hepatic fibrosis, and hepatic fibrosis (Patent Document 1). Furthermore, it has been disclosed that a compound which acts on Edg-1 ($S1P_1$), Edg-3 ($S1P_3$), or Edg-5 is effective as a treatment and a preventive agent for respiratory illnesses such as chronic bronchial asthma, diffuse pulmonary hamartoangiomyomatosis, adult respiratory distress syndrome (ARDS), chronic obstructive pulmonary disease (COPD), pneumonitis, idiopathic interstitial pneumonia, lung cancer, and pneumonia hypersensitivity (Patent Document 2). Furthermore, it has been disclosed that a compound which has an Edg-1 agonistic activity is effective as a treatment and a preventive agent for arteriosclerosis obliterans, thromboangiitis obliterans, Buerger's disease, diabetic neuropathy peripheral arterial disease, septicemia, angiitis, nephritis, pneumonia, cerebral infarction, myocardial infarction, edematous state, arteriosclerosis, varices such as hemorrhoids, anal fissures, and anal fistula, dissecting aortic aneurysm, angina pectoris, DIC, pleurisy, congestive heart failure, multiple organ failure, bedsores, burns, ulcerative colitis, Crohn's disease, heart transplantation, kidney transplantation, skin grafts, liver transplantation, bone marrow transplantation, bone loss, chronic hepatitis, liver cirrhosis, chronic renal failure, and focal glomerular sclerosis (Patent Document 3).

Furthermore, it has been reported that compounds having an S1P receptor agonistic activity regulate leukocyte migration (Non-patent Documents 4 and 5). It has also been disclosed that, in addition to being effective for various organ transplants and GVHD, the series of derivatives introduced in these Non-patent documents are effective for rheumatoid arthritis, lupus nephritis, systemic lupus erythematosus, Hashimoto's disease, multiple sclerosis, myasthenia gravis, type I and II diabetes mellitus, autoimmune diseases such as Crohn's disease, allergic diseases such as atopic dermatitis, allergic rhinitis, allergic conjunctivitis, and allergic contact dermatitis, and inflammatory diseases such as inflammatory bowel disease or ulcerative colitis (Non-patent Documents 4 and 5). Furthermore, a phosphate derivative analogous to what is disclosed in Non-patent Documents 4 and 5 has also been disclosed as an S1P receptor antagonist (Non-patent Document 6). Recently, various compounds, such as amino alcohol derivatives, phosphate derivatives, and carboxylate derivatives, have been disclosed as $S1P_1$ to $S1P_5$ receptor modulators focused on $S1P_1$ receptors, or as immunosuppressive agents (Patent Documents 7 to 62).

Furthermore, since $S1P_4$ receptors are largely concentrated in immunocompetent cells, such as leukocytes, and in organs which greatly contribute to the immune system, it is suggested that $S1P_4$ receptors have a strong contribution to the immune system. In fact, compounds having an $S1P_4$ agonistic activity have been disclosed for autoimmune diseases such as SLE and rheumatism, asthma, allergic diseases such as atopic dermatitis, and inflammatory disease remedies (Patent Documents 30, 35, and 46).

Thus, while a great deal of attention is being paid to S1P receptor agonist drugs which may have hidden potential in a wide variety of medical applications, not all S1P receptor agonist drugs provide a desirable action on the body.

For example, an S1P receptor agonist which has exhibited effectiveness in clinical trials in suppressing organ transplant rejection was found to produce bradycardia as a side effect after administration. This effect was reported to probably be caused by agonistic activity against the $S1P_3$ receptor (Non-patent Documents 6 and 7). Furthermore, agonistic activity against the $S1P_3$ receptor has also been reported to obstruct myocardial blood flow (Non-patent Document 8), and cause cerebral arterial spasms (Non-patent Document 9), and pulmonary edema (Non-patent Document 10).

[Patent Document 1] WO 0198301 pamphlet
[Patent Document 2] WO 03020313 pamphlet
[Patent Document 3] WO 02092068 pamphlet
[Patent Document 4] WO 0218395 pamphlet
[Patent Document 5] WO 02076995 pamphlet
[Patent Document 6] Japanese Patent Application Laid-Open No. 2003-137894
[Patent Document 7] WO 03040097 pamphlet
[Patent Document 8] WO 02064616 pamphlet
[Patent Document 9] WO 02062389 pamphlet
[Patent Document 10] Japanese Patent Application Laid-Open No. 2002-316985
[Patent Document 11] Japanese Patent Application Laid-Open No. 2003-267936
[Patent Document 12] WO 03051876 pamphlet
[Patent Document 13] WO 03061567 pamphlet
[Patent Document 14] WO 03062248 pamphlet
[Patent Document 15] WO 03062252 pamphlet
[Patent Document 16] WO 03073986 pamphlet
[Patent Document 17] WO 03074008 pamphlet
[Patent Document 18] WO 03105771 pamphlet
[Patent Document 19] WO 04010949 pamphlet
[Patent Document 20] WO 04024673 pamphlet
[Patent Document 21] WO 04058149 pamphlet
[Patent Document 22] WO 04071442 pamphlet
[Patent Document 23] WO 04096752 pamphlet
[Patent Document 24] WO 04096757 pamphlet
[Patent Document 25] WO 04103279 pamphlet
[Patent Document 26] WO 04103306 pamphlet
[Patent Document 27] WO 04103309 pamphlet

[Patent Document 28] WO 04110979 pamphlet
[Patent Document 29] WO 04113330 pamphlet
[Patent Document 30] WO 04074297 pamphlet
[Patent Document 31] WO 05014603 pamphlet
[Patent Document 32] WO 05020882 pamphlet
[Patent Document 33] WO 04002531 pamphlet
[Patent Document 34] WO 05032465 pamphlet
[Patent Document 35] WO 05041899 pamphlet
[Patent Document 36] WO 05058848 pamphlet
[Patent Document 37] WO 05070886 pamphlet
[Patent Document 38] WO 05082089 pamphlet
[Patent Document 39] WO 05082841 pamphlet
[Patent Document 40] WO 05021503 pamphlet
[Patent Document 41] WO 05040091 pamphlet
[Patent Document 42] WO 05085179 pamphlet
[Patent Document 43] WO 05118523 pamphlet
[Patent Document 44] WO 05014525 pamphlet
[Patent Document 45] WO 06020951 pamphlet
[Patent Document 46] WO 06001463 pamphlet
[Patent Document 47] WO 03029184 pamphlet
[Patent Document 48] WO 03029205 pamphlet
[Patent Document 49] WO 04026817 pamphlet
[Patent Document 50] WO 04074297 pamphlet
[Patent Document 51] WO 05021503 pamphlet
[Patent Document 52] Japanese Patent Application Laid-Open No. 2004-307439
[Patent Document 53] Japanese Patent Application Laid-Open No. 2004-307440
[Patent Document 54] Japanese Patent Application Laid-Open No. 2004-307441
[Patent Document 55] Japanese Patent Application Laid-Open No. 2004-307442
[Patent Document 56] WO 06041015 pamphlet
[Patent Document 57] Japanese Patent Application Laid-Open No. 2004-137208
[Patent Document 58] Japanese Patent Application Laid-Open No. 2005-41867
[Patent Document 59] Japanese Patent Application Laid-Open No. 2005-47899
[Patent Document 60] WO 05040091 pamphlet
[Patent Document 61] WO 05063671 pamphlet
[Patent Document 62] WO 05079788 pamphlet
[Non-patent Document 1] Y. Takuma et al., Mol. Cell. Endocrinol., 177, 3 (2001).
[Non-patent Document 2] Y. Igarashi, Ann, N.Y. Acad. Sci., 845, 19 (1998).
[Non-patent Document 3] H. Okazaki et al., Biochem. Biophs. Res. Commun., 190, 1104 (1993).
[Non-patent Document 4] S. Mandala et al., Science, 296, 346 (2002).
[Non-patent Document 5] V. Brinkmann et al., J. Biol. Chem., 277 and 21453 (2002).
[Non-patent Document 6] M. G. Sanna et al., J. Biol. Chem., 279, 13839 (2004).
[Non-patent Document 7] M. Forrest et al., J. Pharmacol. Exp. Ther., 309, 758 (2004).
[Non-patent Document 8] B. Levkau et al., Circulation, 110, 3358 (2004).
[Non-patent Document 9] S. Salomone et al., Eur. J. Pharmacol. 469, 125 (2003).
[None-patent Document 10] Y. Gon et al., PNAS 102, 9270 (2005).

DISCLOSURE OF THE INVENTION

Problems to be Solved by the Invention

It is an object of the present invention to provide an amino phosphate derivative having a weak agonistic activity against S1P$_3$, an excellent agonistic activity against S1P$_1$ and/or S1P$_4$ receptors, and few side effects.

Means for Solving the Problems

As a result of continued intensive research to create a highly safe compound which has an agonistic activity against S1P$_1$ and S1P$_4$ receptors, and a weak agonistic activity against an S1P$_3$ receptor, the present inventors discovered that a novel amino phosphate derivative can achieve the above object, thereby completing the present invention.

Specifically, the present invention relates to:
1) An amino phosphate derivative represented by the general formula (1),

[Chemical formula 1]

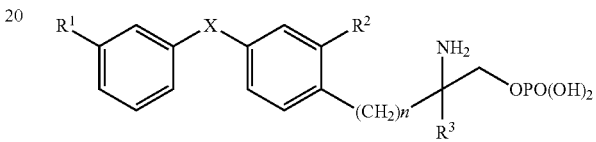

(1)

[wherein R$^1$ represents a chlorine atom or a straight-chain alkyl group having 1 to 3-carbon atoms optionally substituted with halogens, R$^2$ represents a fluorine atom or a chlorine atom, R$^3$ represents a straight-chain alkyl group having 1 to 3 carbon atoms, X represents an oxygen atom or a sulfur atom, and n denotes 2 or 3], or a pharmaceutically acceptable salt or hydrate thereof.

2) The amino phosphate derivative according to 1), wherein the compound represented by the general formula (1) is represented by the general formula (1a),

[Chemical formula 2]

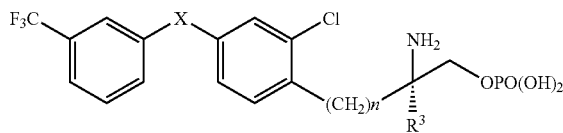

(1a)

[wherein R$^3$, X, and n are as described above], or a pharmaceutically acceptable salt or hydrate thereof.

3) The amino phosphate derivative according to 1) or 2), wherein in the general formula (1) or (1a), R$^3$ is a methyl group, or a pharmaceutically acceptable salt or hydrate thereof.

4) The amino phosphate derivative according to 1), wherein the compound represented by the general formula (1) is,
(R)-2-amino-5-[2-chloro-4-(3-trifluoromethylphenoxy)phenyl]-2-methylpentyl phosphoric acid monoester,
(R)-2-amino-5-[2-chloro-4-(3-trifluoromethylphenylthio)phenyl]-2-methylpentyl phosphoric acid monoester,
(R)-2-amino-4-[2-chloro-4-(3-trifluoromethylphenoxy)phenyl]-2-methylbutyl phosphoric acid monoester,
(R)-2-amino-4-[2-chloro-4-(3-trifluoromethylphenylthio)phenyl]-2-methylbutyl phosphoric acid monoester,
(R)-2-amino-5-[2-chloro-4-(3-ethylphenylthio)phenyl]-2-methylpentyl phosphoric acid monoester,
(R)-2-amino-5-[2-chloro-4-(3-trifluoromethylphenylthio)phenyl]-2-methylpentyl phosphoric acid monoester, or (R)-2-amino-5-[2-chloro-4-(3-trifluoromethylphenylthio)phenyl]-2-propylpentyl phosphoric acid monoester, or a pharmaceutically acceptable salt or hydrate thereof.

5) The amino phosphate derivative according to 1) which is produced by a step of allowing a compound represented by the general formula (2),

[Chemical formula 3]

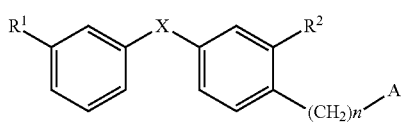

(2)

[wherein $R^1$ represents a chlorine atom or a straight-chain alkyl group having 1 to 3-carbon atoms optionally substituted with halogens, $R^2$ represents a fluorine atom or a chlorine atom, A represents a halogen atom, X represents an oxygen atom or a sulfur atom, and n denotes 2 or 3], and a compound represented by the general formula (12),

[Chemical formula 4]

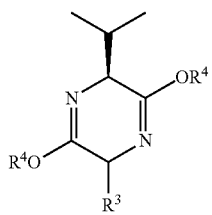

(12)

[wherein $R^3$ represents a straight-chain alkyl group having 1 to 3 carbon atoms and $R^4$ represents an alkyl group having 1 to 6 carbon atoms] to act in the presence of a base, a step of subjecting the resultant product to acid decomposition, protecting a nitrogen atom with a t-butoxycarbonyl group, and then reducing the product, a step of reacting the reduction product with a compound represented by the general formula (10), $$P(OR^6)_3 \quad (10)$$

[wherein $R^6$ represents an alkyl group having 1 to 6 carbon atoms or a benzyl group], and a step of subjecting the resultant product obtained by the previous steps to acidolysis or a halogenosilane treatment, or a pharmaceutically acceptable salt or hydrate thereof.

6) An S1P receptor modulator comprising the amino phosphate derivative, or a pharmaceutically acceptable salt or hydrate thereof, according to any of 1) to 5) as an active ingredient.

7) A pharmaceutical comprising the amino phosphate derivative, or a pharmaceutically acceptable salt or hydrate thereof, according to any of 1) to 5) as an active ingredient.

Effect of the Invention

The present invention has led to the discovery of a novel amino phosphate derivative having an excellent S1P receptor modulatory action. A compound having such an S1P receptor modulatory action is effective as a treatment agent and a preventive agent for arteriosclerosis, arteriosclerosis obliterans, thromboangiitis obliterans, renal fibrosis, hepatic fibrosis, chronic bronchial asthma, diffuse pulmonary hamartoangiomyomatosis, adult respiratory distress syndrome (ARDS), chronic obstructive pulmonary disease (COPD), pneumonitis, idiopathic interstitial pneumonia, lung cancer, pneumonia hypersensitivity, Buerger's disease, diabetic neuropathy peripheral arterial disease, septicemia, angiitis, nephritis, pneumonia, cerebral infarction, myocardial infarction, edematous state, varices, dissecting aortic aneurysm, angina pectoris, DIC, pleurisy, congestive heart failure, multiple organ failure, bedsores, burns, ulcerative colitis, Crohn's disease and the like. Furthermore, a compound having such an S1P receptor modulatory action is effective as a treatment and a preventive agent for rejection of heart transplants, kidney transplants, skin grafts, liver transplants, and bone marrow transplants, and is also an effective as a treatment and a preventive agent for rheumatoid arthritis, lupus nephritis, systemic lupus erythematosus, Hashimoto's disease, multiple sclerosis, myasthenia gravis, diabetes mellitus, atopic dermatitis, allergic rhinitis, allergic conjunctivitis, allergic contact dermatitis and the like.

BEST MODE FOR CARRYING OUT THE INVENTION

In the present invention, the straight-chain alkyl group having 1 to 3 carbon atoms of $R^1$ and $R^3$ is a methyl group, an ethyl group, or an n-propyl group.

In the present invention, the halogen in the "lower alkyl group having 1 to 3 carbon atoms optionally substituted with halogens" of $R^1$ is a fluorine atom or a chlorine atom.

From the perspective of obtaining high safety, $R^1$ is preferably an ethyl group, a propyl group, or a trifluoromethyl group, and more preferably is a trifluoromethyl group. Furthermore, $R^3$ is preferably a methyl group, and n is preferably 3.

Furthermore, from the perspective of obtaining high agonistic activity against the $S1P_1$ receptor, X is preferably a sulfur atom, and the configuration of $R^3$ is preferably a configuration produced as the main product via the below-described synthesis route B (using the compound (12)).

In the present invention, examples of pharmaceutically acceptable salts include alkali metal salts such as sodium salts, potassium salts, magnesium salts, calcium salts, and aluminum salts.

According to the present invention, the compound represented by the general formula (1) can be produced, for example, via the route A shown below.

<Synthesis Route A>

[Chemical formula 5]

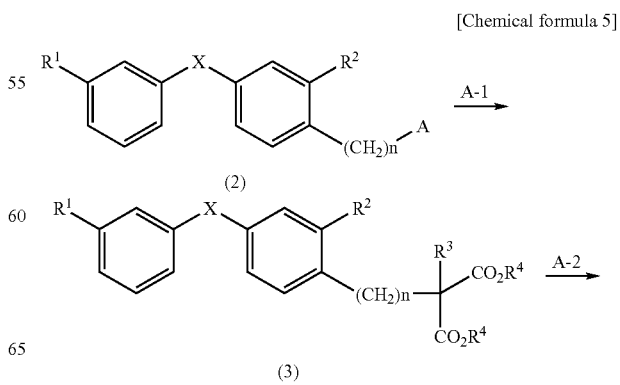

-continued

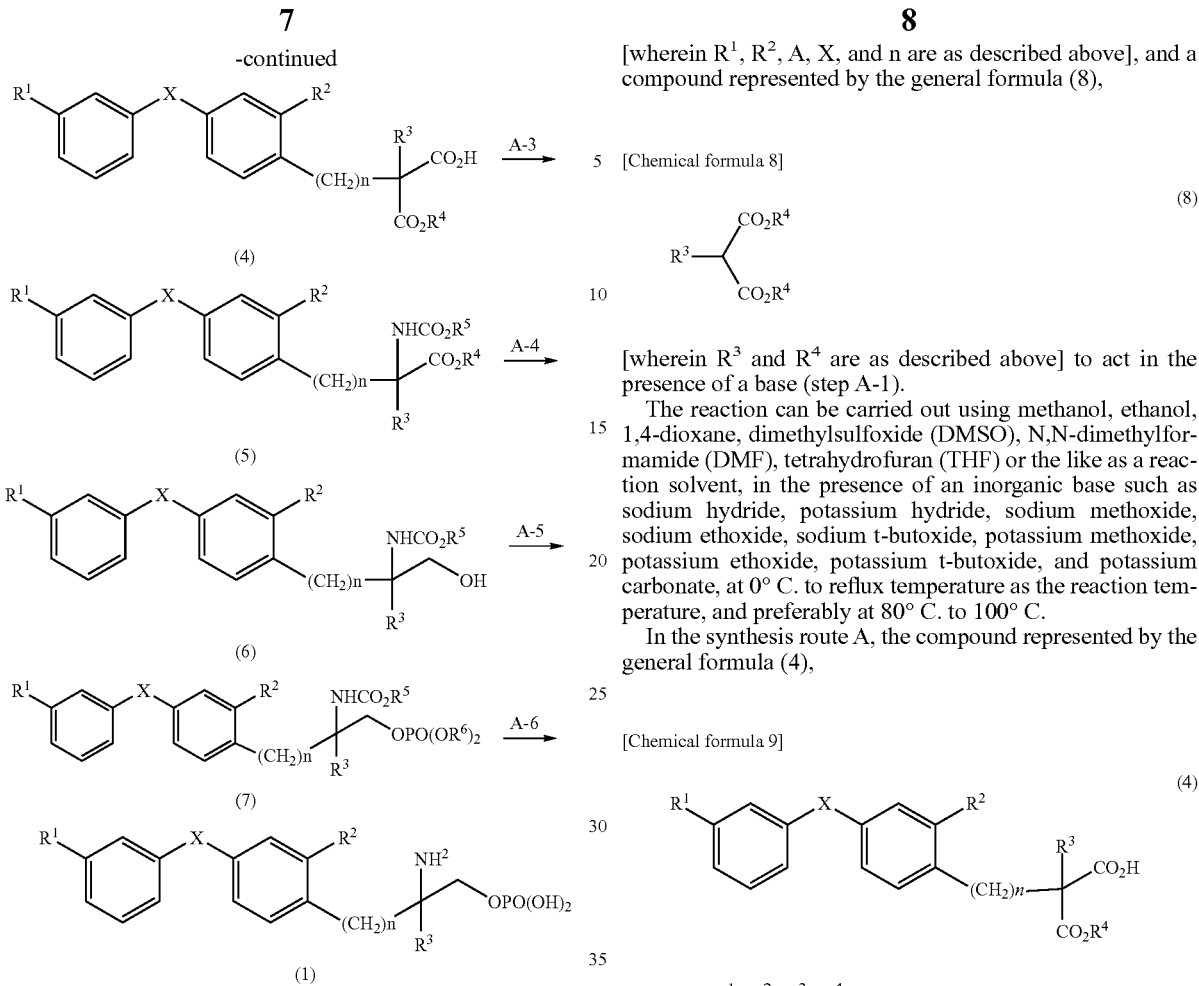

In the synthesis route A, the compound represented by the general formula (3),

[Chemical formula 6]

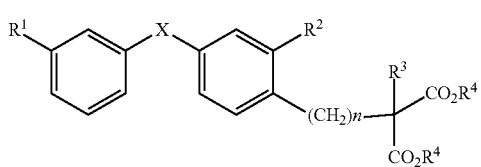

[wherein $R^1$, $R^2$, $R^3$, $R^4$, X, and n are as described above], can be produced by allowing a compound represented by the general formula (2),

[Chemical formula 7]

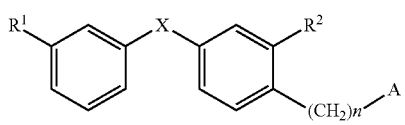

[wherein $R^1$, $R^2$, A, X, and n are as described above], and a compound represented by the general formula (8),

[Chemical formula 8]

[wherein $R^3$ and $R^4$ are as described above] to act in the presence of a base (step A-1).

The reaction can be carried out using methanol, ethanol, 1,4-dioxane, dimethylsulfoxide (DMSO), N,N-dimethylformamide (DMF), tetrahydrofuran (THF) or the like as a reaction solvent, in the presence of an inorganic base such as sodium hydride, potassium hydride, sodium methoxide, sodium ethoxide, sodium t-butoxide, potassium methoxide, potassium ethoxide, potassium t-butoxide, and potassium carbonate, at 0° C. to reflux temperature as the reaction temperature, and preferably at 80° C. to 100° C.

In the synthesis route A, the compound represented by the general formula (4),

[Chemical formula 9]

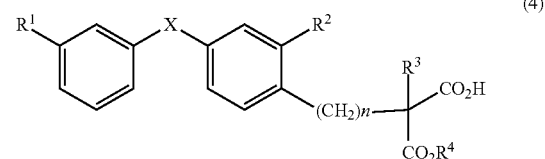

[wherein $R^1$, $R^2$, $R^3$, $R^4$, X, and n are as described above], can be produced by hydrolyzing the compound represented by the general formula (3) (step A-2).

The reaction can be carried out in the presence of a base such as aqueous sodium hydroxide, aqueous potassium hydroxide, and aqueous lithium hydroxide, using methanol, ethanol, 1,4-dioxane, DMF, DMSO, THF or the like as a reaction solvent, at a reaction temperature of 0° C. to reflux temperature. The reaction is especially preferably carried out using potassium hydroxide as the base, in an ethanol solvent, by reacting at 50° C.

Although the compound according to the present invention is preferably an optically-active compound, the optical resolution timing is not especially limited. At this stage, optical resolution may be carried out by HPLC using a chiral column, whereby the desired compound having a chiral center can be obtained.

In the synthesis route 1, the compound represented by the general formula (5),

[Chemical formula 10]

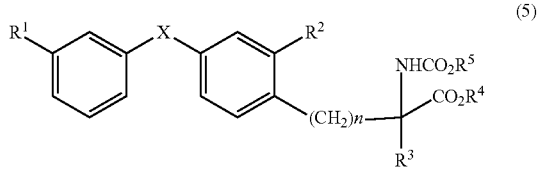

[wherein $R^5$ represents an alkyl group having 1 to 6 carbon atoms, and $R^1$, $R^2$, $R^3$, $R^4$, X, and n are as described above], can be produced by subjecting the compound represented by the general formula (4) to Curtius rearrangement (step A-3).

In the reaction, typical techniques for converting a carboxyl group into a carbamate may be employed. For example, a technique which combines, for example, chloroethyl carbonate and $NaN_3$, or oxalyl chloride and $NaN_3$, or a technique which uses only diphenylphosphoryl azide (DPPA) may be utilized. The reaction is preferably carried out by, after heating diphenylphosphoryl azide to reflux in the presence of an organic base, such as triethylamine, in benzene or toluene solvent, charging the resultant product with an alcohol represented by the general formula (9),

$$R^5OH \quad (9)$$

[wherein $R^5$ is as described above], and continuing to heat the resultant solution under stirring, or after removing the benzene or toluene by distillation, reacting by heating to reflux using the alcohol represented by the general formula (9) as a reaction solvent (step A-3).

At this stage, optical resolution may be carried out by HPLC using a chiral column, whereby the desired compound having a chiral center can be obtained.

In the synthesis route A, the compound represented by the general formula (6),

[Chemical formula 11]

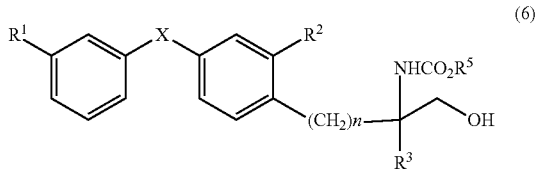

(6)

[wherein $R^1$, $R^2$, $R^3$, $R^5$, X, and n are as described above], can be produced by reducing the compound represented by the general formula (5) (step A-4).

The reaction can be carried out using borane, an alkyl borane derivative like 9-borabicyclo[3.3.1]nonane (9-BBN), or a metal hydride complex compound, such as diisobutylaluminum hydride (($iBu$)$_2$AlH), sodium borohydride ($NaBH_4$), lithium borohydride ($LiBH_4$), and lithium aluminum hydride ($LiAlH_4$), preferably $LiBH_4$, using THF, 1,4-dioxane, ethanol, or methanol as a reaction solvent, at a temperature of 0° C. to reflux temperature, and preferably at room temperature.

Furthermore, at this stage, optical resolution may be carried out by HPLC using a chiral column, whereby the desired compound having a chiral center can be obtained.

In the synthesis route A, the compound represented by the general formula (7),

[Chemical formula 12]

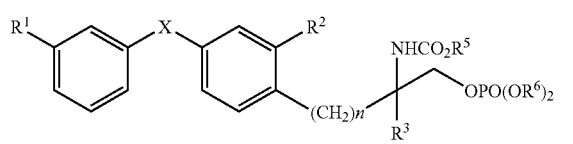

(7)

[wherein $R^6$ represents an alkyl group having 1 to 6 carbon atoms or a benzyl group, and $R^1$, $R^2$, $R^3$, $R^5$, X, and n are as described above], can be produced by reacting the compound represented by the general formula (6) with a compound represented by the general formula (10), $$P(OR^6)_3 \quad (10),$$

[wherein $R^6$ is as described above] (step A-5).

The reaction may be carried out in the presence of carbon tetrabromide and pyridine, without a solvent or using a small amount of a solvent such as methylene chloride, chloroform, acetonitrile, ethyl acetate, THF, and ether, at 0° C. to room temperature.

Furthermore, at this stage, optical resolution may be carried out by HPLC using a chiral column, whereby the desired compound having a chiral center can be obtained.

In the synthesis route A, the compound represented by the general formula (1) can be produced by subjecting the compound represented by the general formula (7) to acidolysis or by treating it with a halogenosilane such as trimethylsilyl bromide or trimethylsilyl iodide (step A-6).

In the case of an acidolysis reaction, the reaction can be carried out in an inorganic acid such as hydrochloric acid or hydrobromic acid, or in a mixed solution of an organic solvent such as methanol or ethanol and an inorganic acid, under heating to reflux. Furthermore, preferably methylene chloride or acetonitrile is used as the reaction solvent, and trimethylsilyl bromide or trimethylsilyl iodide are used at a temperature of 0° C. to room temperature, or trimethylsilyl chloride and sodium bromide or sodium iodide are allowed to act.

In the synthesis route A, among the compounds represented by the general formula (5), compounds in which $R^5$ represents a t-butyl group, specifically, a compound represented by the general formula (5a),

[Chemical formula 13]

(5a)

[wherein Boc represents a t-butoxycarbonyl group, and $R^1$, $R^2$, $R^3$, $R^4$, X, and n are as described above], among the compounds represented by the general formula (6) in the synthesis route A, a compound in which $R^5$ represents a t-butyl group, specifically, a compound represented by the general formula (6a),

[Chemical formula 14]

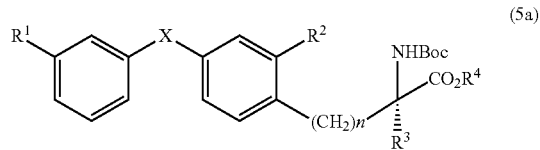

(6a)

[wherein $R^1$, $R^2$, $R^3$, X, Boc, and n are as described above], and among the compounds represented by the general formula (7) in the synthesis route A, a compound in which $R^5$ represents a t-butyl group, specifically, a compound represented by the general formula (7a),

[Chemical formula 15]

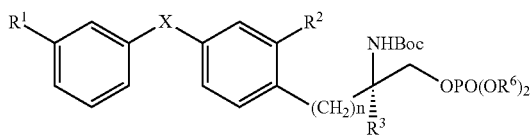

[wherein $R^1$, $R^2$, $R^3$, $R^6$, X, Boc, and n are as described above], can be produced by the synthesis route B.

<Synthesis Route B>

[Chemical formula 16]

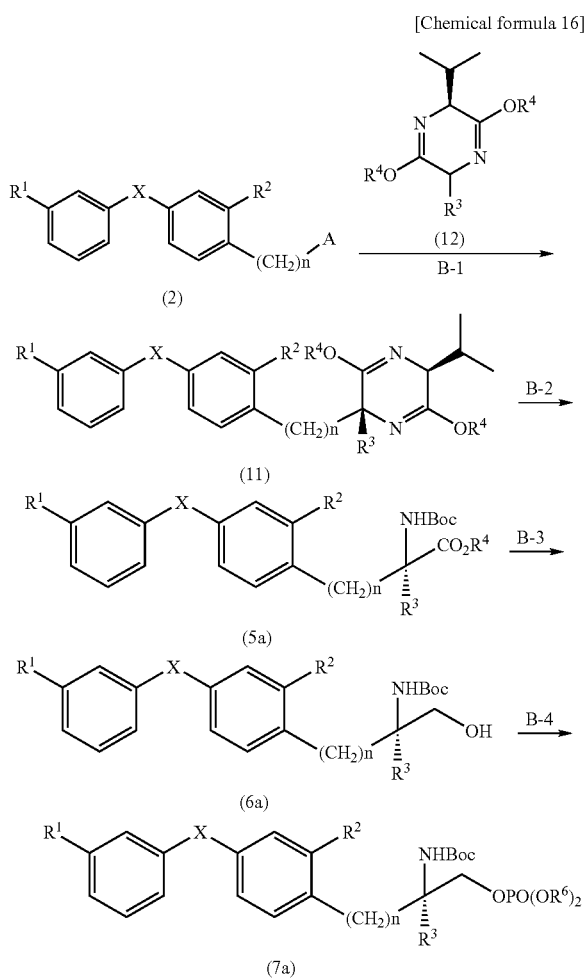

In the synthesis route B, the compound represented by the general formula (11),

[Chemical formula 17]

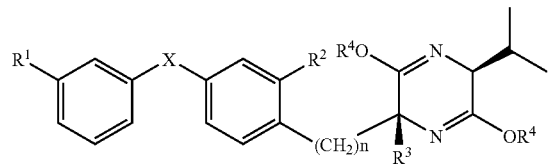

[wherein $R^1$, $R^2$, $R^3$, $R^4$, X, and n are as described above], can be produced by allowing the compound represented by the general formula (2) and a compound represented by the general formula (12),

[Chemical formula 18]

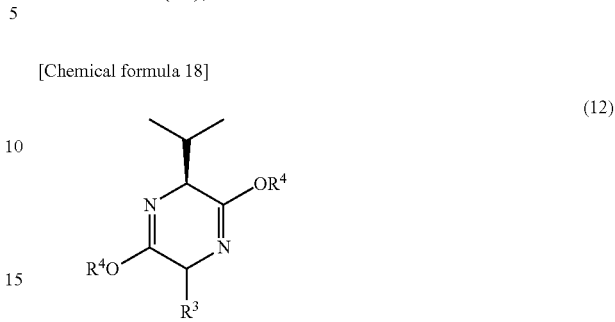

[wherein $R^3$ and $R^4$ are as described above] to act in the presence of a base (step B-1)

The reaction can be carried out using a reaction solvent such as 1,4-dioxane, THF, and ether, using a base such as n-butyllithium and lithium diisopropyl amide, preferably n-butyllithium, and treating a compound represented by the general formula (12) at −78° C., then allowing a compound represented by the general formula (2) to act at −78° C., and reacting while gradually increasing the temperature to room temperature.

In the synthesis route B, the compound represented by the general formula (5a) can be produced by subjecting the compound represented by the general formula (11) to acid decomposition, and then protecting the nitrogen atom with a t-butoxycarbonyl group (Boc group) (step B-2).

It is preferred to carry out the reaction using methanol, ethanol, THF, 1,4-dioxane, or ethyl acetate in which hydrochloric acid is dissolved, and preferably 1,4-dioxane containing hydrochloric acid, by reacting at reflux temperature, then neutralizing with a base to obtain an amino ester, and then using ethylacetate, THF, DMF, 1,4-dioxane, methylenechloride, chloroform, methanol, ethanol, acetonitrile or the like as a solvent, allowing it to act with $Boc_2O$ at 0° C. to room temperature.

In the synthesis route B, the compound represented by the general formula (6a) can be produced by reducing the compound represented by the general formula (5a) (step B-3).

The reaction can be carried out using borane, an alkyl borane derivative like 9-BBN, or a metal hydride complex compound, such as $(iBu)_2AlH$, $NaBH_4$, $LiBH_4$, and $LiAlH_4$, preferably $LiBH_4$, using THF, 1,4-dioxane, ethanol, or methanol as a reaction solvent, at a temperature of 0° C. to reflux temperature, and preferably at room temperature.

In the synthesis route B, the compound represented by the general formula (7a) can be produced by reacting the compound represented by the general formula (6a) and the compound represented by the general formula (10) (step B-4).

The reaction may be carried out in the presence of carbon tetrabromide and pyridine, without a solvent or using a small amount of a solvent such as methylene chloride, chloroform, acetonitrile, ethyl acetate, THF, and ether, at 0° C. to room temperature.

It is noted that concerning the synthesis method of the compound represented by the general formula (2), the compound may be produced by the methods described in the respective pamphlets of WO 03029184, WO 03029205, WO 04026817, WO 04074297, and WO 050444780.

The compound according to the present invention is effective as a treatment agent and a preventive agent for arteriosclerosis, arteriosclerosis obliterans, thromboangiitis obliterans, renal fibrosis, hepatic fibrosis, chronic bronchial asthma, diffuse pulmonary hamartoangiomyomatosis, adult respiratory distress syndrome (ARDS), chronic obstructive pulmonary disease (COPD), pneumonitis, idiopathic interstitial pneumonia, lung cancer, pneumonia hypersensitivity, Buerger's disease, diabetic neuropathy peripheral arterial disease, septicemia, angiitis, nephritis, pneumonia, cerebral infarction, myocardial infarction, edematous state, varices, dissecting aortic aneurysm, angina pectoris, DIC, pleurisy, congestive heart failure, multiple organ failure, bedsores, burns, ulcerative colitis, Crohn's disease and the like. Furthermore, the compound according to the present invention is effective as a treatment and a preventive agent for rejection of heart transplants, kidney transplants, skin grafts, liver transplants, and bone marrow transplants, and is also an effective as a treatment and a preventive agent for rheumatoid arthritis, lupusnephritis, systemic lupus erythematosus, Hashimoto's disease, multiple sclerosis, myasthenia gravis, diabetes mellitus, atopic dermatitis, allergic rhinitis, allergic conjunctivitis, allergic contact dermatitis and the like.

In the case of using as above, the required dose of course depends on the administration method, the specific condition to be treated, and the desired effects. However, generally, a daily dose of about 0.03 to 2.5 mg per kg of body weight is preferred. For mammals such as humans, the recommended daily dose is in the range of about 0.5 mg to about 100 mg. Preferably, administration is carried out in divided doses of four times or less per day, or in retard form. A suitable unit dose form for oral administration includes about 1 to 50 mg of active ingredient.

The compound of the present invention may be administered by an arbitrary conventional route, especially enterally, for example orally, for example in the form of a tablet or a capsule, or parenterally, for example in the form of an injectable solution or a suspension, locally, for example in the form of a lotion, a gel, an ointment, or a cream, or nasally or in the form of a suppository. A pharmaceutical composition containing the compound of the present invention in free form or a pharmaceutically acceptable salt thereof together with at least one kind of pharmaceutically acceptable carrier or diluent may be produced by a conventional method of mixing with the pharmaceutically acceptable carrier or diluent.

The present invention can express even higher effects by using together with an immunosuppressive agent and/or a pharmaceutical which has an anti-inflammatory activity based on another mechanism. Examples of substances which can be used together include immunosuppressive agents used in the treatment and prevention of acute or chronic rejection of allogeneic transplants and heterologous transplants, inflammatory diseases, and autoimmune diseases, immunosuppressive agents having an immunomodulatory activity and/or anti-inflammatory agents having an anti-inflammatory or malignant cell growth inhibition activity. Specific examples include the calcineurin inhibitors cyclosporin A and FK506, the mTOR inhibitors rapamycin, 40-O-(2-hydroxymethyl)-rapamycin, CCI779, and ABT578, the ascomycins ABT281 and ASM981 which have an immunosuppressive activity, mycophenolic acid, mycophenolate mofetil, azathioprine, mizoribine, cyclophosphamide and the like. Further examples include the antifolate methotrexate, adrenal cortical steroids which exhibit broad anti-inflammatory activity, auranofin, actarit, mesalazine, or sulfasalazine and the like which have an immunomodulatory activity, infliximab which is an anti-TNFα antibody, MRA which is an anti-IL-6 receptor antibody, natalizumab which is an anti-integrin antibody and the like.

EXAMPLES

Next, the present invention will be described with the following specific examples. However, the present invention is not limited by these examples.

Furthermore, as the intermediates and the like represented by the general formula (2), the compounds in the pamphlets of WO 03029184, WO 03029205, WO 04026817, WO 04074297, and WO 050444780 may be utilized. Furthermore, (5S)-3,6-diethoxy-5-isopropyl-2-methyl-2,5-dihydropyrazine, (5S)-3,6-dimethoxy-5-isopropyl-2-methyl-2,5-dihydropyrazine, and (5S)-2-allyl-3,6-diethoxy-5-isopropyl-2,5-dihydropyrazine may be synthesized according to Ulrich Shollkopf et. al, Synthesis 969 (1981) and Chunrong Ma et. al., J. Org. Chem., 66, 4525 (2001). Intermediates and the like which were newly synthesized based on the experiment procedures described in these reference documents will now be described as the following reference examples.

Reference Example 1

O-3-(difluoromethyl)phenyldimethylcarbamothioate

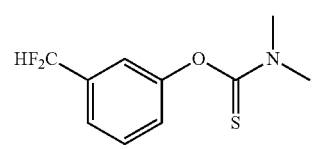

[Chemical formula 19]

1,4-diazabicyclo[2.2.2]octane (9.03 g) and dimethylthiocarbamoyl chloride (9.95 g) were added into a solution of 3-difluoromethylphenol (6.44 g) in N,N-dimethylformamide (149 mL), and the resultant solution was stirred for 4 hours at room temperature. Water was added into the reaction mixture, extracted with ethyl acetate, washed with water and saturated brine in that order, and then dried over anhydrous sodium sulfate. The solvent was removed by distillation, and the resultant residue was purified by silica gel column chromatography (hexane:ethyl acetate=3:1) to obtain the target product (7.04 g) as a colorless oil.

$^1$H-NMR (CDCl$_3$, 400 MHz): δ 3.36 (3H, s), 3.46 (3H, s), 6.66 (1H, t, J=57 Hz), 7.19 (1H, dt, J=7.9, 1.2 Hz), 7.23 (1H, br s), 7.39 (1H, d, J=7.9 Hz), 7.48 (1H, t, J=7.9 Hz).

EIMS (+): 231 [M]$^+$.

Reference Example 2

S-3-(difluoromethyl)phenyldimethylcarbamothioate

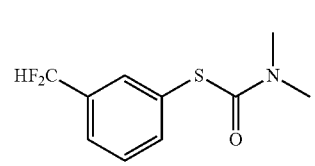

[Chemical formula 20]

A solution of the compound of Reference Example 1 (2.34 g) in diphenyl ether (12 g) was stirred at 250° C. for 2.5 hours. The temperature of the reaction solution was returned to room temperature, and the resultant residue was purified by silica gel column chromatography (hexane:ethyl acetate=3:2) to obtain the target product (1.92 g) as a yellow oil.

$^1$H-NMR (CDCl$_3$, 400 MHz): δ 3.04 (3H, s), 3.10 (3H, s), 6.65 (1H, t, J=57 Hz), 7.48 (1H, t, J=7.9 Hz), 7.54 (1H, d, J=7.9 Hz), 7.61 (1H, t, J=7.9 Hz), 7.64 (1H, s).

EIMS (+): 231 [M]$^+$.

Reference Example 3

2-Chloro-4-(3-difluoromethylphenylthio)benzaldehyde

[Chemical formula 21]

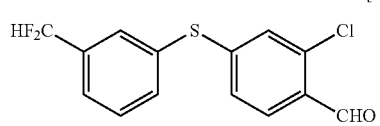

A solution of the compound of Reference Example 2 (4.17 g) in diethyl ether (12 mL) was added dropwise under ice cooling to a solution of lithium aluminum hydride (959 mg) in diethyl ether (48 mL). The resultant solution was then stirred for 20 minutes under ice cooling. 0.5 mol/L hydrochloric acid (30 mL) was added to the reaction mixture, extracted with diethyl ether, washed with water and saturated brine in that order, and then dried over anhydrous sodium sulfate. The solvent was evaporated, and the resultant residue was reacted with 2-chloro-4-fluorobenzaldehyde according to the same experiment procedures as in Reference Example 1 of the pamphlet of WO 03029184 to obtain the target product as a colorless powder.

$^1$H-NMR (CDCl$_3$, 400 MHz) δ 6.67 (1H, t, J=56 Hz), 7.09 (1H, dd, J=7.9, 1.8 Hz), 7.16 (1H, d, J=7.9 Hz), 7.53-7.64 (3H, m), 7.68 (1H, s), 7.79 (1H, d, J=7.9 Hz), 10.37 (1H, s)

EIMS (+): 298 [M]$^+$.

Reference Example 4

2-Fluoro-4-(3-trifluoromethylphenylthio)benzaldehyde

[Chemical formula 22]

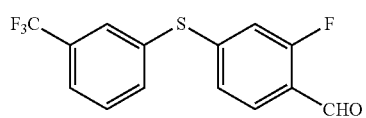

Under an argon atmosphere, ethyldiisopropylamine (7.0 mL), tris(dibenzylideneacetone) dipalladium(0) chloroform adduct (518 mg), xantphos (578 mg), and 3-trifluordmethylthiophenol (3.56 g) were added at room temperature into a solution of 4-bromo-2-fluorobenzaldehyde (4.06 g) in 1,4-dioxane (42 mL), and the resultant solution was heated to reflux for 5 hours. Water was added to the reaction mixture, extracted with ethyl acetate, washed with water and saturated brine in that order, and then dried over anhydrous sodium sulfate. The solvent was evaporated, and the resultant residue was purified by silica gel column chromatography (hexane:ethyl acetate 30:1) to obtain the target product (4.08 g) as a colorless oil.

$^1$H-NMR (CDCl$_3$, 400 MHz): δ 6.86 (1H, dd, J=10, 1.8 Hz), 7.02 (1H, dd, J=7.9, 1.8 Hz), 7.58 (1H, t, J=7.9 Hz), 7.68-7.73 (2H, m), 7.76 (1H, t, J=7.9 Hz), 7.80 (1H, s), 10.26 (1H, s)

EIMS (+): 300 [M]$^+$.

Reference Example 5

2-Chloro-4-(3-chlorophenylthio)benzaldehyde

[Chemical formula 23]

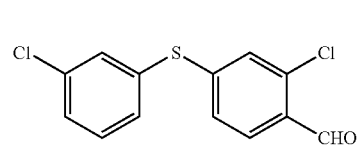

3-Chlorobenzenethiol and 2-chloro-4-fluorobenzaldehyde were reacted according to the same experiment procedures as in Reference Example 1 of the pamphlet of WO 03029205 to obtain the target product as a colorless oil.

$^1$H-NMR (CDCl$_3$, 400 MHz): δ 7.11 (1H, dd, J=9.2, 1.8 Hz), 7.17 (1H, d, J=1.8 Hz), 7.36-7.44 (3H, m), 7.52 (1H, t, J=1.8 Hz), 7.80 (1H, d, J=7.9 Hz), 10.37 (1H, s)

EIMS (+): 282 [M]$^+$.

Reference Example 6

2-Chloro-4-(3-methylphenoxy)benzaldehyde

[Chemical formula 24]

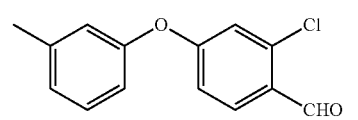

m-Cresol and 2-chloro-4-fluorobenzaldehyde were reacted according to the same experiment procedures as in Reference Example 1 of the pamphlet of WO 03029184 to obtain the target product as a colorless powder.

$^1$H-NMR (CDCl$_3$, 400 MHz): δ 2.38 (3H, s), 6.87-6.96 (4H, m), 7.07 (1H, d, J=7.3 Hz), 7.31 (1H, t, J=7.6 Hz), 7.90 (1H, d, J=8.6 Hz), 10.36 (1H, s).

EIMS (+): 246 [M]$^+$.

Reference Example 7

2-Chloro-4-(3-ethylphenylthio)benzaldehyde

[Chemical formula 25]

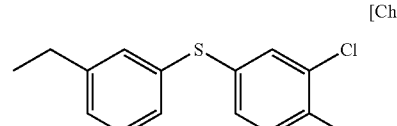

3-Ethylbenzenethiol and 2-chloro-4-fluorobenzaldehyde were reacted according to the same experiment procedures as in Reference Example 1 of the pamphlet of WO 03029205 to obtain the target product as a colorless oil.

¹H-NMR (CDCl₃, 400 MHz): δ 1.26 (3H, t, J=7.3 Hz), 2.680 (2H, q, J=7.3 Hz), 7.04-7.11 (2H, m), 7.28-7.40 (4H, m), 7.76 (1H, d, J=8.6 Hz), 10.35 (1H, s).
EIMS (+): 276 [M]⁺.

Reference Example 8

2-Chloro-4-(3-propylphenoxy)benzaldehyde

[Chemical formula 26]

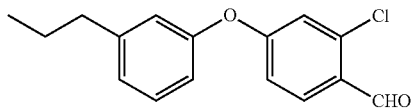

3-Propylphenol and 2-chloro-4-fluorobenzaldehyde were reacted according to the same experiment procedures as in Reference Example 1 of the pamphlet of WO 03029184 to obtain the target product as a pale brown oil.
¹H-NMR (CDCl₃, 400 MHz): δ 0.95 (3H, t, J=7.3 Hz), 1.62-1.68 (2H, m), 2.61 (2H, t, J=7.3 Hz), 6.89-6.94 (3H, m), 6.96 (1H, d, J=2.1 Hz), 7.08 (1H, d, J=7.9 Hz), 7.31-7.35 (1H, m), 7.90 (1H, d, J=8.9 Hz), 10.36 (1H, d, J=0.6 Hz).
EIMS (+): 274 [M]⁺.

Reference Example 9

[2-Chloro-4-(3-ethylphenylthio)phenyl]acetaldehyde

[Chemical formula 27]

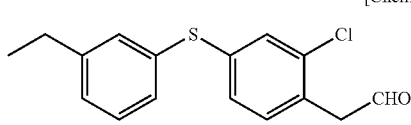

The compound of Reference Example 7 was reacted according to the same experiment procedures as in Reference Example 326 of the pamphlet of WO 04074297 to obtain the target product as a pale yellow oil.

Reference Example 10

Ethyl 3-[2-chloro-4-(3-ethylphenylthio)phenyl]acrylate

[Chemical formula 28]

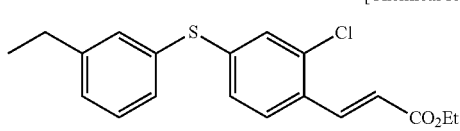

The compound of Reference Example 7 was reacted according to the same experiment procedures as in Reference Example 10 of the pamphlet of WO 03029205 to obtain the target product as a pale yellow oil.
EIMS (+): 346 [M]⁺.

Reference Example 11

3-[2-Chloro-4-(3-ethylphenylthio)phenyl]propan-1-ol

[Chemical formula 29]

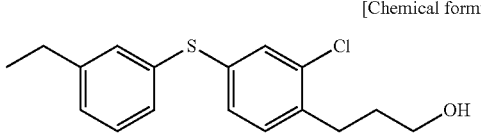

The compound of Reference Example 10 was reacted according to the same experiment procedures as in Reference Example 19 of the pamphlet of WO 03029205, and the resultant product was then reduced according to the same experiment procedures as in Reference Example 35 of the pamphlet of WO 03029205, to obtain the target product as a colorless oil.
¹H-NMR (CDCl₃, 400 MHz): δ 1.22 (3H, t, J=7.3 Hz), 1.84-1.90 (2H, m), 2.62 (2H, q, J=7.6 Hz), 2.78-2.82 (2H, m), 3.69 (2H, t, J=6.1 Hz), 7.10-7.18 (4H, m), 7.23-7.29 (3H, m).

Reference Example 12

3-[2-Chloro-4-(3-propylphenoxy)phenyl]propan-1-ol

[Chemical formula 30]

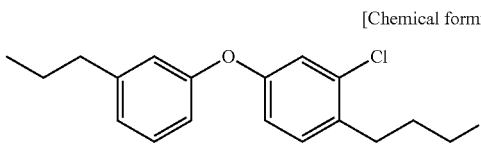

The compound of Reference Example 8 was successively reacted according to the same experiment procedures as in Reference Example 10 and then Reference Example 11 to obtain the target product as a colorless oil.
¹H-NMR (CDCl₃, 400 MHz): δ 0.94 (3H, t, J=7.3 Hz), 1.37 (1H, br s), 1.58-1.68 (2H, m), 1.85-1.92 (2H, m), 2.57 (2H, t, J=7.6 Hz), 2.80 (2H, t, J=7.6 Hz), 3.70 (2H, dt, J=6.1, 4.6 Hz), 6.80-6.85 (3H, m), 6.95 (1H, d, J=7.9 Hz), 7.00 (1H, d, J=2.8 Hz), 7.17 (1H, d, J=8.3 Hz), 7.24 (1H, t, J=7.9 Hz).
EIMS (+): 304 [M]⁺.

Reference Example 13

3-[2-Fluoro-4-(3-trifluoromethylphenylthio)phenyl]propan-1-ol

[Chemical formula 31]

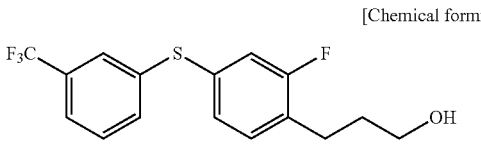

The compound of Reference Example 4 was successively reacted according to the same experiment procedures as in Reference Example 10 and then Reference Example 11 to obtain the target product as a colorless oil.

$^1$H-NMR (CDCl$_3$, 400 MHz): δ 1.88 (2H, tt, J=6.7, 6.1 Hz), 2.75 (2H, t, J=6.7 Hz), 3.69 (2H, t, J=6.1 Hz), 7.05 (1H, dd, J=10, 1.8 Hz), 7.10 (1H, dd, J=7.9, 1.8 Hz), 7.20 (1H, t, J=7.9 Hz), 7.38-7.51 (3H, m), 7.55 (1H, s).

Reference Example 14

3-[2-Chloro-4-(3-chlorophenylthio)phenyl]propan-1-ol

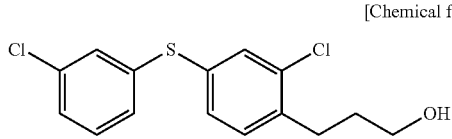

[Chemical formula 32]

The compound of Reference Example 5 was successively reacted according to the same experiment procedures as in Reference Example 10 and then Reference Example 11 to obtain the target product as a colorless oil.

$^1$H-NMR (CDCl$_3$, 400 MHz): δ 1.33 (1H, br s), 1.83-1.95 (2H, m), 2.81-2.85 (2H, m), 3.70 (2H, br s), 7.15-7.23 (5H, m), 7.24-7.29 (1H, m), 7.38 (1H, d, J=1.8 Hz).

Reference Example 15

3-[2-Chloro-4-(3-methylphenoxy)phenyl]propan-1-ol

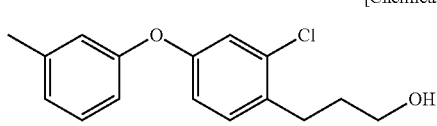

[Chemical formula 33]

The compound of Reference Example 6 was successively reacted according to the same experiment procedures as in Reference Example 10 and then Reference Example 11 to obtain the target product as a colorless oil.

$^1$H-NMR (CDCl$_3$, 400 MHz): δ 1.31 (1H, brs), 1.87-1.90 (2H, m), 2.34 (3H, s), 2.80 (2H, t, J=7.3 Hz), 3.70 (2H, dd, J=11.6, 6.1 Hz), 6.79-6.86 (3H, m), 6.94 (1H, d, J=7.3 Hz), 6.99 (1H, d, J=2.4 Hz), 7.18 (1H, d, J=7.9 Hz), 7.22 (1H, t, J=7.3 Hz).

EIMS (+): 276 [M]$^+$.

Reference Example 16

3-[2-Chloro-4-(3-difluoromethylphenylthio)phenyl]propan-1-ol

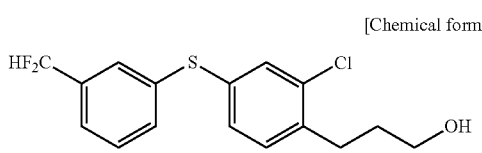

[Chemical formula 34]

The compound of Reference Example 3 was successively reacted according to the same experiment procedures as in Reference Example 10 and then Reference Example 11 to obtain the target product as a colorless oil.

$^1$H-NMR (CDCl$_3$, 400 MHz): δ 1.32 (1H, t, J=4.9 Hz), 1.85-1.93 (2H, m), 2.81-2.85 (2H, m), 3.70 (2H, q, J=6.7 Hz), 6.59 (1H, t, J=56 Hz), 7.17-7.23 (2H, m), 7.36-7.41 (4H, m), 7.45 (1H, s).

Reference Example 17

2-Chloro-4-(3-ethylphenylthio)-1-(2-iodoethyl)benzene

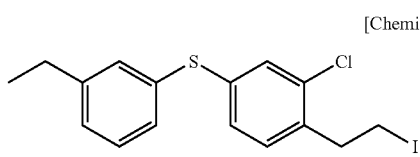

[Chemical formula 35]

The compound of Reference Example 9 was reacted according to the same experiment procedures as in Reference Example 327 of the pamphlet of WO 04074297 to obtain the target product as a colorless oil.

$^1$H-NMR (CDCl$_3$, 400 MHz): δ 1.22 (3H, t, J=7.3 Hz), 2.63 (2H, q, J=7.3 Hz), 3.23-3.28 (2H, m), 3.32-3.35 (2H, m), 7.09-7.29 (7H, m).

EIMS (+): 402 [M]$^+$.

Reference Example 18

2-Chloro-4-(3-ethylphenylthio)-1-(3-iodopropyl)benzene

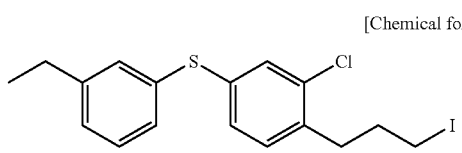

[Chemical formula 36]

The compound of Reference Example 11 was reacted according to the same experiment procedures as in Reference Example 164 of the pamphlet of WO 03029184 to obtain the target product as a colorless oil.

$^1$H-NMR (CDCl$_3$, 400 MHz): δ 1.22 (3H, t, J=7.3 Hz), 2.12 (2H, quintet, J=7.3 Hz), 2.63 (2H, q, J=7.3 Hz), 2.81 (2H, t, J=7.3 Hz), 3.19 (2H, t, J=7.3 Hz), 7.09-7.19 (4H, m), 7.24-7.28 (3H, m).

EIMS (+): 416 [M]$^+$.

Reference Example 19

2-Chloro-1-(3-iodopropyl)-4-(3-propylphenoxy)benzene

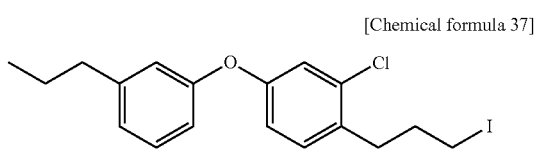

[Chemical formula 37]

The compound of Reference Example 12 was reacted according to the same experiment procedures as in Reference Example 164 of the pamphlet of WO 03029184 to obtain the target product as a pale yellow oil.

¹H-NMR (CDCl₃, 400 MHz): δ 0.94 (3H, t, J=7.3 Hz), 1.60-1.68 (2H, m), 2.10-2.17 (2H, m), 2.57 (2H, t, J=7.6 Hz), 2.81 (2H, t, J=7.6 Hz), 3.21 (2H, t, J=7.0 Hz), 6.80-6.85 (3H, m), 6.96 (1H, d, J=7.9 Hz), 6.99 (1H, d, J=2.4 Hz), 7.19 (1H, d, J=8.3 Hz), 7.25 (1H, t, J=7.9 Hz).

EIMS (+): 414 [M]⁺.

Reference Example 20

2-Fluoro-1-(3-iodopropyl)-4-(3-trifluoromethylphenylthio)benzene

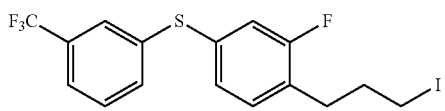

[Chemical formula 38]

The compound of Reference Example 13 was reacted according to the same experiment procedures as in Reference Example 164 of the pamphlet of WO 03029184 to obtain the target product as a colorless oil.

¹H-NMR (CDCl₃, 400 MHz): δ 2.13 (2H, quintet, J=7.3 Hz), 2.76 (2H, t, J=7.3 Hz), 3.18 (2H, t, J=6.7 Hz), 7.03 (1H, dd, J=10, 1.8 Hz), 7.09 (1H, dd, J=7.9, 1.8 Hz), 7.20 (1H, t, J=7.9 Hz), 7.39-7.52 (3H, m), 7.57 (1H, s).

EIMS (+): 404 [M]⁺.

Reference Example 21

2-Chloro-4-(3-chlorophenylthio)-1-(3-iodopropyl)benzene

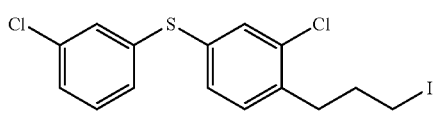

[Chemical formula 39]

The compound of Reference Example 14 was reacted according to the same experiment procedures as in Reference Example 164 of the pamphlet of WO 03029184 to obtain the target product as a colorless oil.

¹H-NMR (CDCl₃, 400 MHz): δ 2.14 (2H, tt, J=7.3, 6.7 Hz), 2.84 (2H, t, J=7.3 Hz), 3.20 (2H, t, J=6.7 Hz), 7.16-7.25 (5H, m), 7.28 (1H, t, J=1.8 Hz), 7.36 (1H, d, J=1.8 Hz).

EIMS (+): 422 [M]⁺.

Reference Example 22

2-Chloro-1-(3-iodopropyl)-4-(3-methylphenoxy)benzene

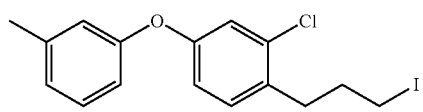

[Chemical formula 40]

The compound of Reference Example 15 was reacted according to the same experiment procedures as in Reference Example 164 of the pamphlet of WO 03029184 to obtain the target product as a yellow oil.

¹H-NMR (CDCl₃, 400 MHz): δ 2.13 (2H, quint, J=7.3 Hz), 2.34 (3H, s), 2.81 (2H, t, J=7.3 Hz), 3.21 (2H, t, J=7.3 Hz), 6.81-6.84 (3H, m), 6.95 (1H, d, J=7.9 Hz), 6.99 (1H, d, J=2.4 Hz), 7.18 (1H, d, J=7.9 Hz), 7.23 (1H, t, J=7.9 Hz).

EIMS (+): 386 [M]⁺.

Reference Example 23

2-Chloro-4-(3-difluoromethylphenylthio)-1-(3-iodopropyl)benzene

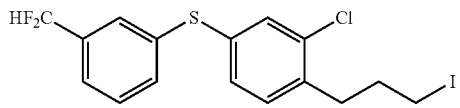

[Chemical formula 41]

The compound of Reference Example 16 was reacted according to the same experiment procedures as in Reference Example 164 of the pamphlet of WO 03029184 to obtain the target product as a colorless oil.

¹H-NMR (CDCl₃, 400 MHz): δ 2.10-2.17 (2H, m), 2.84 (2H, t, J=7.3 Hz), 3.20 (2H, t, J=6.7 Hz), 6.60 (1H, t, J=56 Hz), 7.18 (1H, dd, J=7.9, 1.2 Hz), 7.22 (1H, d, J=7.9 Hz), 7.36 (1H, d, J=1.2 Hz), 7.41 (3H, d, J=1.2 Hz), 7.47 (1H, s).

Example 1

(2R,5S)-2-[2-chloro-4-(3-trifluoromethylphenoxy)phenyl]propyl-3,6-diethoxy-5-isopropyl-2-methyl-2,5-dihydropyrazine

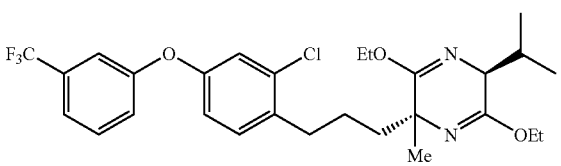

[Chemical formula 42]

Under an argon atmosphere, a solution of n-butyllithium in hexane (1.54 mol/L, 3.59 mL) was added at −78° C. into a solution of (5S)-3,6-diethoxy-5-isopropyl-2-methyl-2,5-dihydropyrazine (905 mg) in THF (16 mL), and the resultant solution was stirred at −78° C. for 30 minutes. Next, A solution of 2-chloro-1-(3-iodopropyl)-4-(3-trifluoromethylphenoxy)benzene (2.47 g) in THF (4 mL) was added to the reaction mixture, and the resultant solution was stirred at −78° C. for 30 minutes and then at 0° C. for 1 hour. Water was added to the reaction mixture, extracted with ethyl acetate, washed with water and saturated brine in that order, and then dried over anhydrous sodium sulfate. The solvent was evaporated, and the resultant residue was purified by silica gel column chromatography (hexane:ethyl acetate=60:1) to obtain the target product (1.59 g) as a colorless oil.

$^1$H-NMR (CDCl$_3$, 400 MHz): δ 0.70 (3H, d, J=6.7 Hz), 1.05 (3H, d, J=6.7 Hz), 1.18-1.50 (9H, m), 1.32 (3H, s), 1.86-1.97 (1H, m), 2.21-2.30 (1H, m), 2.65 (2H, t, J=7.6 Hz), 3.90 (1H, d, J=2.1 Hz), 3.97-4.21 (4H, m), 6.84 (1H, dd, J=7.9, 2.4 Hz), 7.00 (1H, d, J=2.4 Hz), 7.15 (2H, d, J=7.9 Hz), 7.24 (1H, br s), 7.36 (1H, d, J=7.9 Hz), 7.44 (1H, t, J=7.9 Hz).

Example 2

(2R,5S)-2-[2-chloro-4-(3-trifluoromethylphenylthio)phenyl]propyl-3,6-diethoxy-5-isopropyl-2-methyl-2,5-dihydropyrazine

[Chemical formula 43]

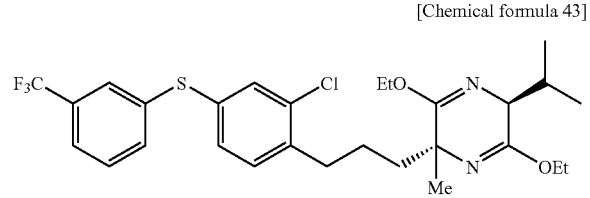

(5S)-3,6-diethoxy-5-isopropyl-2-methyl-2,5-dihydropyrazine and 2-chloro-1-(3-iodopropyl)-4-(3-trifluoromethylphenylthio)benzene were reacted in the same manner as in Example 1 to obtain the target product as a colorless oil.

$^1$H-NMR (CDCl$_3$, 400 MHz): δ 0.63 (3H, d, J=6.7 Hz), 1.07 (3H, d, J=6.7 Hz), 1.18-1.29 (10H, m), 1.34-1.66 (2H, m), 1.79-1.91 (1H, m), 2.25-2.33 (1H, m), 2.70 (2H, t, J=7.6 Hz), 3.85 (1H, br s), 3.99-4.23 (4H, m), 7.16 (2H, d, J=7.9 Hz), 7.20 (1H, dd, J=7.9, 1.8 Hz), 7.36-7.42 (3H, m), 7.44-7.50 (1H, m), 7.52 (1H, br s).

Example 3

(2R,5S)-2-[2-chloro-4-(3-trifluoromethylphenoxy)phenyl]ethyl-3,6-diethoxy-5-isopropyl-2-methyl-2,5-dihydropyrazine

[Chemical formula 44]

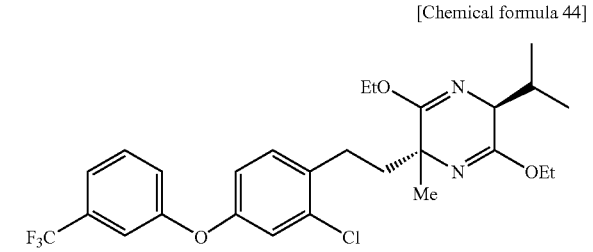

(5S)-3,6-diethoxy-5-isopropyl-2-methyl-2,5-dihydropyrazine and 2-chloro-1-(2-iodoethyl)-4-(3-trifluoromethylphenoxy)benzene were reacted in the same manner as in Example 1 to obtain the target product as a colorless oil.

$^1$H-NMR (CDCl$_3$, 400 MHz): δ 0.72 (3H, d, J=6.7 Hz), 1.08 (3H, d, J=6.7 Hz), 1.29 (6H, t, J=7.3 Hz), 1.36 (3H, s), 1.74-1.82 (1H, m), 2.13-2.20 (1H, m), 2.25-2.32 (1H, m), 2.39-2.56 (2H, m), 3.95 (1H, d, J=3.1 Hz), 4.02-4.22 (4H, m), 6.83 (1H, dd, J=8.6, 2.4 Hz), 6.99 (1H, d, J=2.4 Hz), 7.12-7.15 (2H, m), 7.23 (1H, br s), 7.35 (1H, d, J=7.8 Hz), 7.44 (1H, t, J=7.8 Hz).

EIMS (+): 524 [M]$^+$.

Example 4

(2R,5S)-2-[2-chloro-4-(3-trifluoromethylphenylthio)phenyl]ethyl-3,6-diethoxy-5-isopropyl-2-methyl-2,5-dihydropyrazine

[Chemical formula 45]

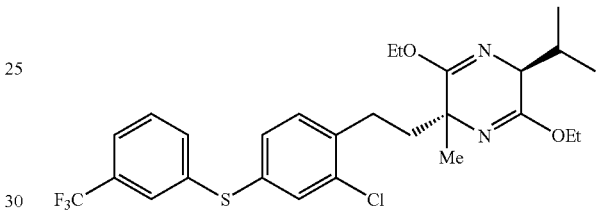

(5S)-3,6-diethoxy-5-isopropyl-2-methyl-2,5-dihydropyrazine and 2-chloro-1-(2-iodoethyl)-4-(3-trifluoromethylphenylthio)benzene were reacted in the same manner as in Example 1 to obtain the target product as a colorless oil.

$^1$H-NMR (CDCl$_3$, 400 MHz): δ 0.72 (3H, d, J=6.7 Hz), 1.08 (3H, d, J=6.7 Hz), 1.28 (6H, t, J=7.3 Hz), 1.35 (3H, s), 1.68-1.90 (1H, m), 2.10-2.19 (1H, m), 2.38-2.57 (1H, m), 3.95 (1H, d, J=3.1 Hz), 4.02-4.22 (4H, m), 7.13 (1H, d, J=7.9 Hz), 7.18 (1H, dd, J=7.9, 2.4 Hz), 7.35-7.42 (3H, m), 7.43-7.48 (1H, m), 7.54 (1H, br s).

Example 5

(2R,5S)-2-[2-chloro-4-(3-ethylphenylthio)phenyl]ethyl-3,6-diethoxy-5-isopropyl-2-methyl-2,5-dihydropyrazine

[Chemical formula 46]

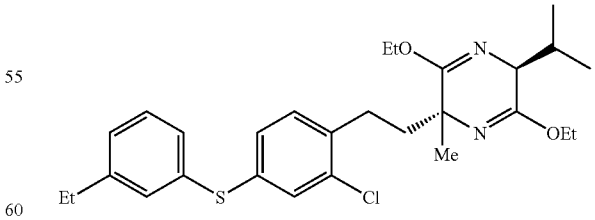

(5S)-3,6-diethoxy-5-isopropyl-2-methyl-2,5-dihydropyrazine and the compound of Reference Example 17 were reacted in the same manner as in Example 1 to obtain the target product as a colorless oil.

$^1$H-NMR (CDCl$_3$, 400 MHz): δ 0.72 (3H, d, J=6.7 Hz), 1.07 (3H, d, J=6.7 Hz), 1.21 (3H, t, J=7.3 Hz), 1.28 (3H, t,

J=7.3 Hz), 1.29 (3H, t, J=7.3 Hz), 1.34 (3H, s), 1.70-1.79 (1H, m), 2.09-2.16 (1H, m), 2.24-2.32 (1H, m), 2.35-2.52 (2H, m), 2.61 (2H, q, J=7.3 Hz), 3.95 (1H, d, J=3.1 Hz), 4.03-4.20 (4H, m), 7.04-7.15 (4H, m), 7.21-7.26 (3H, m).

ESIMS (+): 501 [M+H]$^+$.

Example 6

(2R,5S)-2-[2-chloro-4-(3-methylphenoxy)phenyl]propyl-3,6-dimethoxy-5-isopropyl-2-methyl-2,5-dihydropyrazine

[Chemical formula 47]

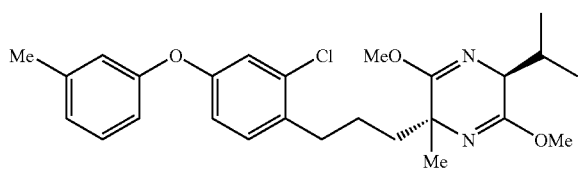

(5S)-3,6-dimethoxy-5-isopropyl-2-methyl-2,5-dihydropyrazine and the compound of Reference Example 22 were reacted in the same manner as in Example 1 to obtain the target product as a colorless oil.

$^1$H-NMR (CDCl$_3$, 400 MHz): δ 0.68 (3H, d, J=6.7 Hz), 1.07 (3H, d, J=6.7 Hz), 1.33 (3H, s), 1.36-1.43 (1H, m), 1.55-1.62 (1H, m), 1.86-1.92 (1H, m), 2.24-2.26 (1H, m), 2.34 (3H, s), 2.62 (2H, t, J=7.9 Hz), 3.65 (3H, s), 3.66 (3H, s), 3.94 (1H, d, J=3.7 Hz), 6.79-6.82 (3H, m), 6.93 (1H, d, J=7.3 Hz), 6.96 (1H, d, J=2.4 Hz), 7.09 (1H, d, J=7.9 Hz), 7.22 (1H, t, J=7.9 Hz).

EIMS (+): 456 [M]$^+$.

Example 7

(2R,5S)-2-[2-chloro-4-(3-ethylphenylthio)phenyl]propyl-3,6-diethoxy-5-isopropyl-2-methyl-2,5-dihydropyrazine

[Chemical formula 48]

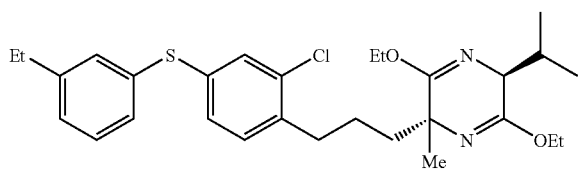

(5S)-3,6-diethoxy-5-isopropyl-2-methyl-2,5-dihydropyrazine and the compound of Reference Example 18 were reacted in the same manner as in Example 1 to obtain the target product as a colorless oil.

$^1$H-NMR (CDCl$_3$, 400 MHz): δ 0.68 (3H, d, J=6.7 Hz), 1.04 (3H, d, J=6.7 Hz), 1.20-1.26 (9H, m), 1.31 (3H, s), 1.36-1.43 (1H, m), 1.50-1.57 (1H, m), 1.85-1.92 (1H, m), 2.21-2.28 (1H, m), 2.60-2.65 (4H, m), 3.88 (1H, d, J=3.7 Hz), 4.00-4.16 (4H, m), 7.06-7.16 (4H, m), 7.22-7.27 (3H, m).

ESIMS (+): 515 [M+H]$^+$.

Example 8

(2R,5S)-2-[2-chloro-4-(3-chlorophenylthio)phenyl]propyl-3,6-diethoxy-5-isopropyl-2-methyl-2,5-dihydropyrazine

[Chemical formula 49]

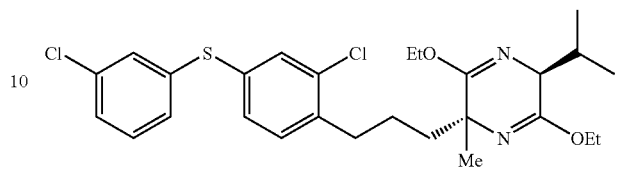

(5S)-3,6-diethoxy-5-isopropyl-2-methyl-2,5-dihydropyrazine and the compound of Reference Example 21 were reacted in the same manner as in Example 1 to obtain the target product as a colorless oil.

$^1$H-NMR (CDCl$_3$, 400 MHz): δ 0.69 (3H, d, J=6.7 Hz), 1.08 (3H, d, J=6.7 Hz), 1.18-1.29 (7H, m), 1.31 (3H, s), 1.34-1.47 (1H, m), 1.50-1.63 (1H, m), 1.85-1.95 (1H, m), 2.20-2.30 (1H, m), 2.65 (2H, t, J=7.6 Hz), 3.89 (1H, d, J=3.1 Hz), 3.99-4.23 (4H, m), 7.11-7.23 (6H, m), 7.35 (1H, d, J=1.8 Hz).

ESIMS (+) 521 [M+H]$^+$.

Example 9

(2R,5S)-2-[2-fluoro-4-(3-trifluoromethylphenylthio)phenyl]propyl-3,6-diethoxy-5-isopropyl-2-methyl-2,5-dihydropyrazine

[Chemical formula 50]

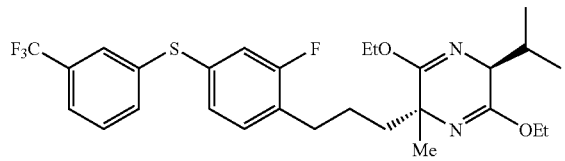

(5S)-3,6-diethoxy-5-isopropyl-2-methyl-2,5-dihydropyrazine and the compound of Reference Example 20 were reacted in the same manner as in Example 1 to obtain the target product as a colorless oil.

$^1$H-NMR (CDCl$_3$, 400 MHz): δ 0.67 (3H, d, J=6.7 Hz), 1.06 (3H, d, J=6.7 Hz), 1.18-1.29 (7H, m), 1.33 (3H, s), 1.36-1.66 (2H, m), 1.85-1.95 (1H, m), 2.23-2.33 (1H, m), 2.67 (2H, t, J=7.6 Hz), 3.89 (1H, d, J=3.1 Hz), 3.99-4.23 (4H, m), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 10

(2S,5S)-2-allyl-2-[2-chloro-4-(3-trifluoromethylphenylthio)phenyl]propyl-3,6-diethoxy-5-isopropyl-2,5-dihydropyrazine

[Chemical formula 51]

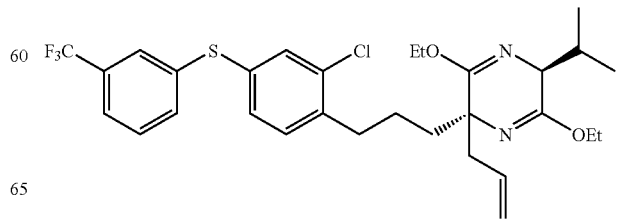

(5S)-2-allyl-3,6-diethoxy-5-isopropyl-2,5-dihydropyrazine and 2-chloro-1-(3-iodopropyl)-4-(3-trifluoromethylphenylthio)benzene were reacted in the same manner as in Example 1 to obtain the target product as a colorless oil.

$^1$H-NMR (CDCl$_3$, 400 MHz): δ 0.67 (3H, d, J=6.7 Hz), 1.05 (3H, d, J=6.7 Hz), 1.23 (3H, t, J=6.4 Hz), 1.25 (3H, t, J=6.4 Hz), 1.30-1.64 (3H, m), 1.80-1.90 (1H, m), 2.23-2.39 (2H, m), 2.53 (1H, dd, J=12.4, 7.3 Hz), 2.65 (2H, t, J=7.6 Hz), 3.83 (1H, d, J=3.1 Hz), 4.03-4.18 (4H, m), 4.92-5.04 (2H, m), 5.60-5.73 (1H, m), 7.13 (2H, d, J=7.9 Hz), 7.18 (1H, dd, J=7.9 Hz, 1.8 Hz), 7.36 (1H, d, J=1.8 Hz), 7.38-7.42 (2H, m), 7.44-7.49 (1H, m), 7.55 (1H, br s).

Example 11

(2R,5S)-2-[2-chloro-4-(3-difluoromethylphenylthio)phenyl]propyl-3,6-diethoxy-5-isopropyl-2-methyl-2,5-dihydropyrazine

[Chemical formula 52]

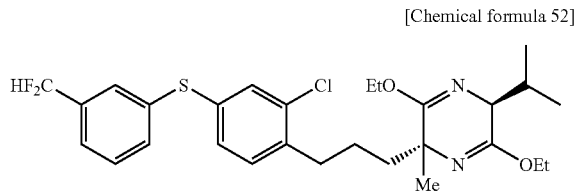

5S)-3,6-diethoxy-5-isopropyl-2-methyl-2,5-dihydropyrazine and the compound of Reference Example 23 were reacted in the same manner as in Example 1 to obtain the target product as a colorless oil.

$^1$H-NMR (CDCl$_3$, 400 MHz): δ 0.70 (3H, d, J=6.7 Hz), 1.06 (3H, d, J=6.7 Hz), 1.20-1.32 (7H, m), 1.33 (3H, s), 1.35-1.48 (1H, m), 1.58-1.60 (1H, m), 1.85-1.95 (1H, m), 2.24-2.32 (1H, m), 2.66 (2H, t, J=7.3 Hz), 3.90 (1H, d, J=3.7 Hz), 3.99-4.22 (4H, m), 6.61 (1H, t, J=56 Hz), 7.14 (1H, d, J=7.9 Hz), 7.19 (1H, dd, J=7.9, 1.8 Hz), 7.36 (1H, d, J=1.8 Hz), 7.39 (3H, s), 7.46 (1H, s).
ESIMS (+): [M+H]$^+$.

Example 12

Ethyl (R)-2-t-butoxycarbonylamino-5-[2-chloro-4-(3-trifluoromethylphenoxy)phenyl]-2-methylpentanoate

[Chemical formula 53]

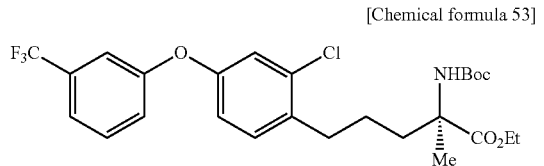

To A solution of the compound of Example 1 (1.59 g) in 1,4-dioxane (60 mL) was added 0.5 mol/L hydrochloric acid (30 mL). The resultant solution was stirred at room temperature for 1 hour, and then left to stand at room temperature overnight. The solution was concentrated, neutralized with saturated aqueous sodium hydrogen carbonate solution, and extracted with ethyl acetate. The extract was washed with water and saturated brine, and then dried over anhydrous sodium sulfate. The extract was concentrated, and the resultant residue was dissolved in acetonitrile (15 mL). To this solution was added di-tert-butoxydicarbonate (1.55 g), and the resultant solution was stirred at room temperature for 4 hours and then left to stand at room temperature overnight. To the reaction solution was added water, extracted with ethyl acetate, washed with water and saturated brine in that order, and then dried over anhydrous sodium sulfate. The solvent was evaporated, and the resultant residue was purified by silica gel column chromatography (hexane ethyl acetate=9:1) to obtain the target product (1.00 g) as a colorless oil.

$^1$H-NMR (CDCl$_3$, 400 MHz): δ 1.26 (3H, t, J=7.3 Hz), 1.43 (9H, s), 1.53 (3H, s), 1.45-1.68 (2H, m), 1.80-1.90 (1H, m), 2.12-2.30 (1H, m), 2.69 (2H, t, J=7.6 Hz), 4.16-4.24 (2H, m), 5.33 (1H, br s), 6.85 (1H, dd, J=7.9 Hz, 2.4 Hz), 7.02 (1H, d, J=2.4 Hz), 7.15 (1H, dd, J=7.9 Hz, 2.4 Hz), 7.17 (1H, d, J=7.9 Hz), 7.24 (1H, br s), 7.37 (1H, d, J=7.9 Hz), 7.45 (1H, t, J=7.9 Hz).

Example 13

Ethyl (R)-2-t-butoxycarbonylamino-5-[2-fluoro-4-(3-trifluoromethylphenylthio)phenyl]-2-methylpentanoate

[Chemical formula 54]

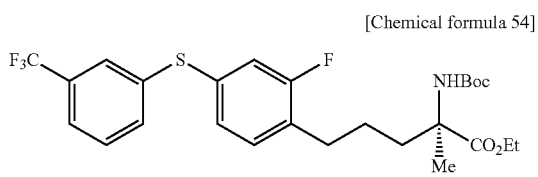

The compound of Example 9 was reacted in the same manner as in Example 12 to obtain the target product as a colorless oil.

$^1$H-NMR (CDCl$_3$, 400 MHz): δ 1.26 (3H, t, J=7.3 Hz), 1.42 (9H, s), 1.51 (3H, s), 1.45-1.68 (2H, m), 1.77-1.86 (1H, m), 2.09-2.20 (1H, m), 2.69 (2H, t, J=7.6 Hz), 4.13-4.23 (2H, m), 5.29 (1H, br s), 7.02 (1H, dd, J=9.8 Hz, 1.8 Hz), 7.08 (1H, dd, J=7.9 Hz, 2.4 Hz), 7.13 (1H, t, J=7.9 Hz), 7.38-7.50 (3H, m), 7.55 (1H, s).

Example 14

Ethyl (S)-2-allyl-2-t-butoxycarbonylamino-5-[2-chloro-4-(3-trifluoromethylphenylthio)phenyl]pentanoate

[Chemical formula 55]

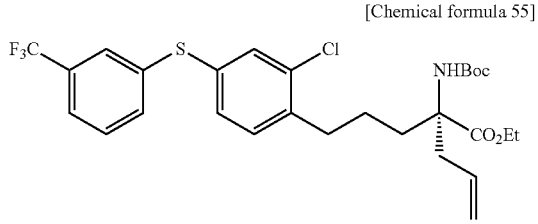

The compound of Example 10 was reacted in the same manner as in Example 12 to obtain the target product as a colorless oil.

¹H-NMR (CDCl₃, 400 MHz) δ 1.24 (3H, t, J=7.3 Hz), 1.29-1.39 (1H, m), 1.43 (9H, s), 1.60-1.70 (1H, m), 1.78-1.86 (1H, m), 2.32-2.50 (2H, m), 2.66-2.73 (2H, m), 2.99-3.10 (1H, m), 4.19 (2H, q), 5.03 (1H, d, J=3.1 Hz), 5.09 (1H, s), 5.49 (1H, br s), 5.54-5.68 (1H, m), 7.16 (1H, d, J=7.9 Hz), 7.19 (1H, dd, J=7.9, 1.8 Hz), 7.35 (1H, d, J=1.8 Hz), 7.39-7.44 (2H, m), 7.45-7.50 (1H, m), 7.54 (1H, br s).

Example 15

Ethyl (R)-2-t-butoxycarbonylamino-5-[2-chloro-4-(3-trifluoromethylphenylthio)phenyl]-2-propylpentanoate

[Chemical formula 56]

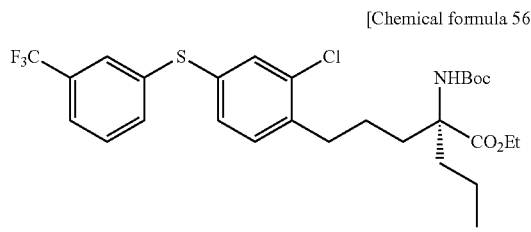

To a solution of the compound of Example 14 (400 mg) in ethyl acetate (20 mL) was added palladium-carbon/ethylene diamine complex (100 mg), and the resultant solution was stirred at room temperature for 24 hours under hydrogen atmosphere. The reaction solution was filtered through Celite, and the solvent was evaporated. The resultant residue was purified by silica gel column chromatography (hexane:ethyl acetate=30:1) to obtain the target product (293 mg) as a colorless oil.

¹H-NMR (CDCl₃, 400 MHz): δ 0.91 (3H, t, J=7.3 Hz), 1.42 (9H, s), 1.15-1.77 (8H, m), 2.72 (2H, t, J=7.3 Hz), 3.63 (1H, d, J=12 Hz), 3.67 (1H, d, J=12 Hz), 4.52 (1H, br s), 7.19-7.22 (2H, m), 7.39 (1H, s), 7.40-7.50 (3H, m), 7.54 (1H, br s).

FABMS (+): 532 [M+H]⁺.

Example 16

(R)-2-t-butoxycarbonylamino-5-[2-chloro-4-(3-trifluoromethylphenoxy)phenyl]-2-methylpentan-1-ol

[Chemical formula 57]

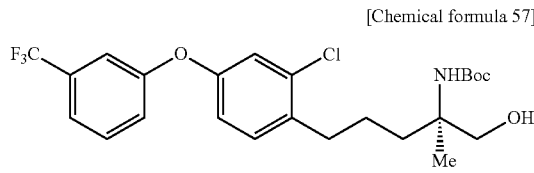

To a solution of the compound of Example 12 (1.00 g) in THF (14 mL) was added under ice cooling lithium borohydride (229 mg), and then ethanol (1.4 mL) was added dropwise. The resultant solution was then stirred for 1 hour under ice cooling. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=4:1) to obtain the target product (910 mg) as a colorless oil.

¹H-NMR (CDCl₃, 400 MHz): δ 1.16 (3H, s), 1.43 (9H, s), 1.53-1.74 (3H, m), 1.81-1.93 (1H, m), 2.73 (2H, t, J=7.3 Hz), 3.61 (1H, d, J=12 Hz), 3.65 (1H, d, J=12 Hz), 4.58 (1H, br s), 4.58 (1H, br s), 6.86 (1H, dd, J=7.9, 2.4 Hz), 7.03 (1H, d, J=2.4 Hz), 7.16 (1H, dd, J=7.9 Hz, 2.4 Hz), 7.21 (1H, d, J=7.9 Hz), 7.24 (1H, br s), 7.37 (1H, d, J=7.9 Hz), 7.45 (1H, t, J=7.9 Hz).

Example 17

(R)-2-t-butoxycarbonylamino-5-[2-chloro-4-(3-trifluoromethylphenylthio)phenyl]-2-methylpentan-1-ol

[Chemical formula 58]

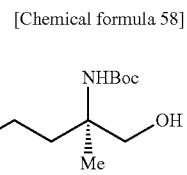

The compound of Example 2 was reacted in the same manner as in Example 12 to obtain an ester, which was then reacted in the same manner as in Example 16 to obtain the target product as a colorless oil.

¹H-NMR (CDCl₃, 400 MHz): δ 1.14 (3H, s), 1.42 (9H, s), 1.48-1.76 (4H, m), 1.81-1.90 (1H, m), 2.74 (2H, t, J=6.7 Hz), 3.61 (1H, d, J=12 Hz), 3.65 (1H, d, J=12 Hz), 4.56 (1H, br s), 4.58 (1H, br s), 7.20 (2H, d, J=1.2 Hz), 7.37-7.50 (4H, m), 7.54 (1H, br s).

Optical Rotation: [α]_D²⁷ +14.31 (c 0.63, CHCl₃).

Example 18

(R)-2-t-butoxycarbonylamino-4-[2-chloro-4-(3-trifluoromethylphenoxy)phenyl]-2-methylbutan-1-ol

[Chemical formula 59]

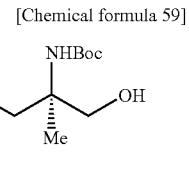

The compound of Example 3 was reacted in the same manner as in Example 12 to obtain an ester, which was then reacted in the same manner as in Example 16 to obtain the target product as a colorless oil.

¹H-NMR (CDCl₃, 400 MHz): δ 1.26 (3H, s), 1.45 (9H, s), 1.80-1.88 (1H, m), 2.05-2.12 (1H, m), 2.66-2.80 (2H, m), 3.68 (1H, d, J=11.6 Hz), 3.73 (1H, d, J=11.6 Hz), 4.70 (1H, br s), 6.86 (1H, dd, J=8.5, 2.5 Hz), 7.03 (1H, d, J=2.5 Hz), 7.13-7.16 (1H, m), 7.22-7.24 (2H, m), 7.37 (1H, d, J=7.9 Hz), 7.45 (1H, t, J=7.9 Hz).

FABMS (+): 474 [M+H]⁺.

Example 19

(R)-2-t-butoxycarbonylamino-4-[2-chloro-4-(3-trifluoromethylphenylthio)phenyl]-2-methylbutan-1-ol

[Chemical formula 60]

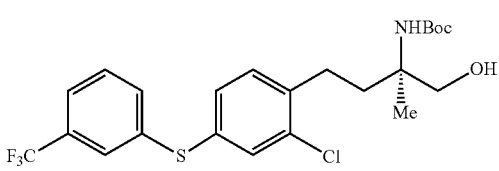

The compound of Example 4 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.25 (3H, s), 1.44 (9H, s), 1.79-1.89 (1H, m), 2.05-2.13 (1H, m), 2.66-2.83 (2H, m), 3.68 (1H, d, J=12 Hz), 3.71 (1H, d, J=12 Hz), 4.69 (1H, br s), 7.20-7.23 (2H, m), 7.37-7.42 (3H, m), 7.45-7.50 (2H, m), 7.55 (1H, br s).

Example 20

(R)-2-t-butoxycarbonylamino-4-[2-chloro-4-(3-ethylphenylthio)phenyl]-2-methylbutan-1-ol

[Chemical formula 61]

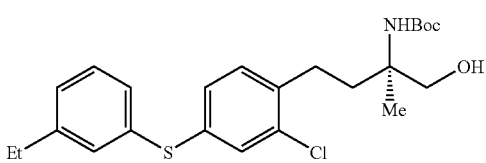

The compound of Example 5 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.22 (3H, t, J=7.3 Hz), 1.24 (3H, s), 1.44 (9H, s), 1.77-1.85 (1H, m), 2.02-2.09 (1H, m), 2.62 (2H, q, J=7.3 Hz), 2.63-2.78 (2H, m), 3.64-3.73 (2H, m), 4.08 (1H, br), 4.68 (1H, br s), 7.10-7.17 (4H, m), 7.22-7.28 (3H, m).

ESIMS (+): 450 [M+H]$^+$.

Example 21

(R)-2-t-butoxycarbonylamino-5-[2-chloro-4-(3-methylphenoxy)phenyl]-2-methylpentan-1-ol

[Chemical formula 62]

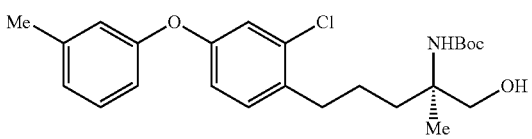

The compound of Example 6 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.15 (3H, s), 1.43 (9H, s), 1.61-1.67 (3H, m), 1.83-1.87 (1H, m), 2.34 (3H, s), 2.70 (2H, t, J=7.0 Hz), 3.62-3.65 (2H, m), 4.57 (1H, s), 6.81-6.84 (3H, m), 6.94 (1H, d, J=7.3 Hz), 6.98 (1H, d, J=3.1 Hz), 7.15 (1H, d, J=7.9 Hz), 7.22 (1H, t, J=7.9 Hz).

ESIMS (+): 434 [M+H]$^+$.

Example 22

(R)-2-t-butoxycarbonylamino-5-[2-chloro-4-(3-ethylphenylthio)phenyl]-2-methylpentan-1-ol

[Chemical formula 63]

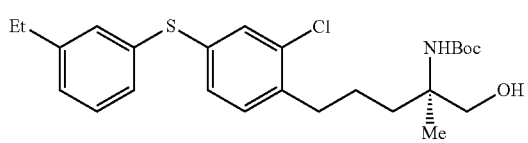

The compound of Example 7 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.14 (3H, s), 1.22 (3H, t, J=7.3 Hz), 1.43 (9H, s), 1.54-1.70 (3H, m), 1.79-1.89 (1H, m), 2.62 (2H, q, J=7.3 Hz), 2.70 (2H, t, J=7.0 Hz), 3.57-3.66 (2H, m), 4.05 (1H, br), 4.55 (1H, br s), 7.10-7.17 (4H, m), 7.17-7.28 (3H, m).

ESIMS (+): 464 [M+H]$^+$.

Example 23

(R)-2-t-butoxycarbonylamino-5-[2-chloro-4-(3-propylphenoxy)phenyl]-2-methylpentan-1-ol

[Chemical formula 64]

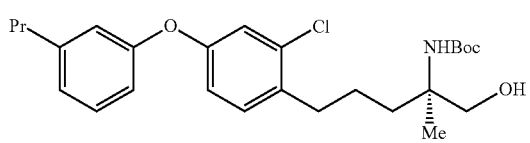

The compound of Reference Example 19 and (5S)-3,6-diethoxy-5-isopropyl-2-methyl-2,5-dihydropyrazine were reacted in the same manner as in Example 1. The resultant compound was reacted in the same manner as in Example 12 to obtain an ester, which was then reacted in the same manner as in Example 16 to obtain the target product as a colorless oil.

$^1$H-NMR (CDCl$_3$, 400 MHz): δ 0.94 (3H, t, J=7.3 Hz), 1.15 (3H, s), 1.24-1.28 (2H, m), 1.43 (9H, s), 1.60-1.69 (3H, m), 1.80-1.90 (1H, m), 2.57 (2H, t, J=7.6 Hz), 2.70 (2H, t, J=7.6 Hz), 3.58-3.67 (2H, m), 4.11 (1H, br s), 4.58 (1H, br s), 6.79-6.85 (3H, m), 6.95 (1H, d, J=7.9 Hz), 6.99 (1H, d, J=2.8 Hz), 7.15 (1H, d, J=8.3 Hz), 7.24 (1H, t, J=7.9 Hz).

Example 24

(R)-2-t-butoxycarbonylamino-5-[2-chloro-4-(3-chlorophenylthio)phenyl]-2-methylpentan-1-ol

[Chemical formula 65]

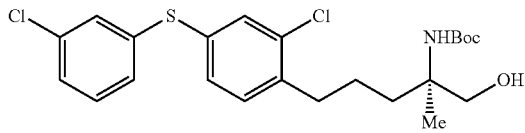

The compound of Example 8 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.14 (3H, s), 1.43 (9H, s), 1.58-1.74 (3H, m), 1.79-1.92 (1H, m), 2.73 (2H, t, J=6.7 Hz), 3.61 (1H, d, J=12 Hz), 3.64 (1H, d, J=12 Hz), 4.08 (1H, br s), 4.57 (1H, br s), 7.17-7.27 (6H, m), 7.37 (1H, s).

ESIMS (+): 470 [M+H]$^+$.

Example 25

(R)-2-t-butoxycarbonylamino-5-[2-fluoro-4-(3-trifluoromethylphenylthio)phenyl]-2-methylpentan-1-ol

[Chemical formula 66]

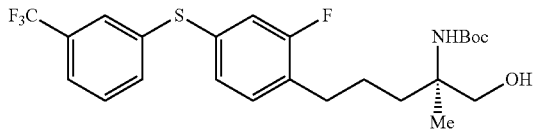

The compound of Example 13 was reacted in the same manner as in Example 16 to obtain the target product as a colorless oil.

$^1$H-NMR (CDCl$_3$, 400 MHz): δ 1.14 (3H, s), 1.42 (9H, s), 1.55-1.74 (3H, m), 1.75-1.85 (1H, m), 2.65 (2H, t, J=6.7 Hz), 3.58-3.64 (2H, m), 4.03 (1H, br s), 4.55 (1H, br s), 7.04 (1H, dd, J=9.8 Hz, 1.8 Hz), 7.10 (1H, dd, J=7.9 Hz, 1.8 Hz), 7.17 (1H, t, J=7.9 Hz), 7.38-7.50 (3H, m), 7.54 (1H, br s).

Example 26

(R)-2-t-butoxycarbonylamino-5-[2-chloro-4-(3-trifluoromethylphenylthio)phenyl]-2-propylpentane-1-ol

[Chemical formula 67]

The compound of Example 15 was reacted in the same manner as in Example 16 to obtain the target product as a colorless oil.

$^1$H-NMR (CDCl$_3$, 400 MHz): δ 0.92 (3H, t, J=7.3 Hz), 1.42 (9H, s), 1.14-1.80 (8H, m), 2.72 (2H, t, J=7.3 Hz), 3.62 (1H, d, J=12 Hz), 3.66 (1H, d, J=12 Hz), 4.54 (1H, br s), 7.16-7.22 (2H, m), 7.39 (1H, s), 7.40-7.48 (3H, m), 7.55 (1H, br s).

FABMS (+): 532 [M+H]$^+$.

Example 27

(R)-2-t-butoxycarbonylamino-5-[2-chloro-4-(3-difluoromethylphenylthio)phenyl]-2-methylpentan-1-ol

[Chemical formula 68]

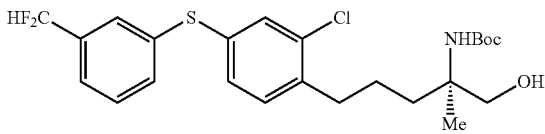

The compound of Example 11 was reacted in the same manner as in Example 12 to obtain an ester, which was then reacted in the same manner as in Example 16 to obtain the target product as a colorless oil.

$^1$H-NMR (CDCl$_3$, 400 MHz): δ 1.14 (3H, s), 1.42 (9H, s), 1.51-1.73 (3H, m), 1.79-1.92 (1H, m), 2.73 (2H, t, J=6.7 Hz), 3.57-3.67 (2H, m), 4.05 (1H, br s), 4.57 (1H, br s), 6.60 (1H, t, J=56 Hz), 7.19 (2H, d, J=1.2 Hz), 7.36 (1H, s), 7.39 (3H, br s), 7.44 (1H, s).

ESIMS (+): 537[M+H]$^+$.

Example 28

(R)-2-t-butoxycarbonylamino-5-[2-chloro-4-(3-trifluoromethylphenoxy)phenyl]-1-dimethoxyphosphoryloxy-2-methylpentane

[Chemical formula 69]

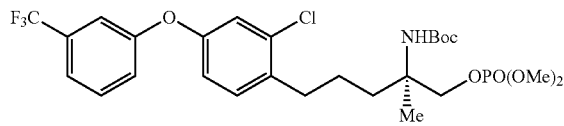

To a solution of the compound of Example 16 (456 mg) in pyridine (5 mL) was added under ice cooling carbon tetrabromide (620 mg) and trimethyl phosphite (219 μL), and the resultant solution was then stirred at 0° C. for 1 hour. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=1:2) to obtain the target product (533 mg) as a colorless oil.

$^1$H-NMR (CDCl$_3$, 400 MHz): δ 1.26 (3H, s), 1.42 (9H, s), 1.52-1.70 (3H, m), 1.86-1.97 (1H, m), 2.71 (2H, t, J=7.6 Hz), 3.78 (6H, d, J=11 Hz), 4.00 (1H, dd, J=9.8, 4.9 Hz), 4.16 (1H, dd, J=9.8, 4.9 Hz), 4.52 (1H, br s), 6.86 (1H, dd, J=7.9, 2.4 Hz), 7.03 (1H, d, J=2.4 Hz), 7.16 (1H, dd, J=7.9, 2.4 Hz), 7.19 (1H, d, J=7.9 Hz), 7.24 (1H, br s), 7.37 (1H, d, J=7.9 Hz), 7.45 (1H, t, J=7.9 Hz).

Example 29

(R)-2-t-butoxycarbonylamino-5-[2-chloro-4-(3-trifluoromethylphenylthio)phenyl]-1-dimethoxyphosphoryloxy-2-methylpentane

[Chemical formula 70]

The compound of Example 17 was reacted in the same manner as in Example 28 to obtain the target product as a colorless oil.

¹H-NMR (CDCl₃, 400 MHz): δ 1.25 (3H, s), 1.42 (9H, s), 1.53-1.68 Hz (3H, m), 1.85-1.97 (1H, m), 2.73 (2H, t, J=7.6 Hz), 3.77 (6H, d, J=11 Hz), 3.98 (1H, dd, J=9.8, 4.9 Hz), 4.15 (1H, dd, J=9.8, 4.9 Hz), 4.52 (1H, br s), 7.18-7.21 (2H, m), 7.38 (1H, d, J=2.4 Hz), 7.40-7.43 (2H, m), 7.46 7.50 (1H, m), 7.54 (1H, br s).

Example 30

(R)-2-t-butoxycarbonylamino-4-[2-chloro-4-(3-trifluoromethylphenoxy)phenyl]-1-dimethoxyphosphoryloxy-2-methylbutane

[Chemical formula 71]

The compound of Example 18 was reacted in the same manner as in Example 28 to obtain the target product as a colorless oil.

¹H-NMR (CDCl₃, 400 MHz): δ 1.38 (3H, s), 1.45 (9H, s), 1.77-1.85 Hz (1H, m), 2.04-2.17 (1H, m), 2.66-2.79 (2H, m), 3.79 (6H, d, J=11 Hz), 4.04 (1H, dd, J=9.8, 4.9 Hz), 4.24 (1H, dd, J=9.8, 4.9 Hz), 4.64 (1H, br s), 6.86 (1H, dd, J=8.5, 2.5 Hz), 7.02 (1H, d, J=2.5 Hz), 7.14-7.16 (1H, m), 7.21 (1H, d, J=8.5 Hz), 7.24 (1H, bs s), 7.36-7.38 (1H, m), 7.45 (1H, t, J=8.0 Hz).

FABMS (+): 582 [M+H]⁺.

Example 31

(R)-2-t-butoxycarbonylamino-4-[2-chloro-4-(3-trifluoromethylphenylthio)phenyl]-1-dimethoxyphosphoryloxy-2-methylbutane

[Chemical formula 72]

The compound of Example 19 was reacted in the same manner as in Example 28 to obtain the target product as a colorless oil.

¹H-NMR (CDCl₃, 400 MHz): δ 1.37 (3H, s), 1.45 (9H, s), 1.74-1.84 (1H, m), 2.06-2.18 (1H, m), 2.64-2.81 (2H, m), 3.79 (6H, d, J=11.0 Hz), 4.03 (1H, dd, J=9.8, 4.9 Hz), 4.23 (1H, dd, J=9.8, 4.9 Hz), 4.64 (1H, br s), 7.20 (2H, d, J=1.2 Hz), 7.38 (1H, d, J=2.4 Hz), 7.40-7.42 (1H, m), 7.42 (1H, d, J=1.2 Hz), 7.45-7.50 (1H, m), 7.55 (1H, br s).

Example 32

(R)-2-t-butoxycarbonylamino-4-[2-chloro-4-(3-ethylphenylthio)phenyl]-1-dimethoxyphosphoryloxy-2-methylbutane

[Chemical formula 73]

The compound of Example 20 was reacted in the same manner as in Example 28 to obtain the target product as a colorless oil.

¹H-NMR (CDCl₃, 400 MHz): δ 1.22 (3H, t, J=7.3 Hz), 1.36 (3H, s), 1.44 (9H, s), 1.73-1.81 (1H, m), 2.06-2.18 (1H, m), 2.64 (2H, q, J=7.3 Hz), 2.65-2.76 (2H, m), 3.78 (6H, d, J=11.0 Hz), 4.03 (1H, dd, J=9.8, 4.9 Hz), 4.22 (1H, dd, J=9.8, 4.9 Hz), 4.62 (1H, br s), 7.09-7.17 (4H, m), 7.22-7.27 (3H, m).

ESIMS (+): 558 [M+H]⁺.

Example 33

(R)-2-t-butoxycarbonylamino-5-[2-chloro-4-(3-methylphenoxy)phenyl]-1-dimethoxyphosphoryloxy-2-methylpentane

[Chemical formula 74]

The compound of Example 21 was reacted in the same manner as in Example 28 to obtain the target product as a yellow oil.

¹H-NMR (CDCl₃, 400 MHz): δ 1.26 (3H, s), 1.42 (9H, s), 1.58-1.65 (3H, m), 1.89-1.91 (1H, m), 2.34 (3H, s), 2.69 (2H, t, J=7.3 Hz), 3.77 (6H, t, J=11.0 Hz), 4.00 (1H, dd, J=9.8, 4.9 Hz), 4.15 (1H, dd, J=9.8, 4.9 Hz), 4.52 (1H, brs), 6.79-6.84 (3H, m), 6.94 (1H, d, J=7.3 Hz), 6.98 (1H, d, J=2.4 Hz), 7.13 (1H, d, J=7.9 Hz), 7.22 (1H, t, J=7.9 Hz).

ESIMS (+): 542 [M+H]⁺.

Example 34

(R)-2-t-butoxycarbonylamino-5-[2-chloro-4-(3-ethylphenylthio)phenyl]-1-dimethoxyphosphoryloxy-2-methylpentane

[Chemical formula 75]

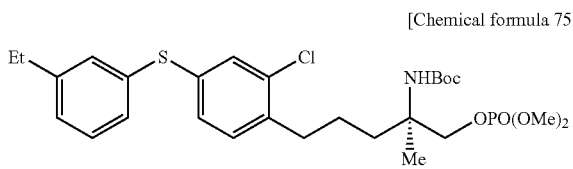

The compound of Example 22 was reacted in the same manner as in Example 28 to obtain the target product as a colorless oil.

$^1$H-NMR (CDCl$_3$, 400 MHz): δ 1.22 (3H, t, J=7.3 Hz), 1.26 (3H, s), 1.41 (9H, s), 1.53-1.65 (3H, m), 1.84-1.93 (1H, m), 2.63 (2H, q, J=7.3 Hz), 2.66-2.71 (2H, m), 3.76 (3H, d, J=11.0 Hz), 3.78 (3H, d, J=11.0 Hz), 3.98 (1H, dd, J=9.8, 4.9 Hz), 4.14 (1H, dd, J=9.8, 4.9 Hz), 4.50 (1H, br s), 7.11-7.27 (7H, m).

ESIMS (+): 572 [M+H]$^+$.

Example 35

(R)-2-t-butoxycarbonylamino-5-[2-chloro-4-(3-propylphenoxy)phenyl]-1-dimethoxyphosphoryloxy-2-methylpentane

[Chemical formula 76]

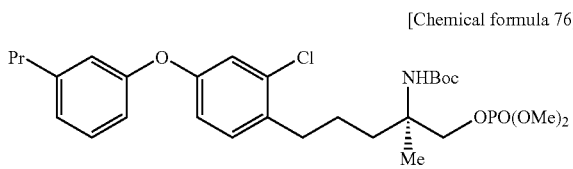

The compound of Example 23 was reacted in the same manner as in Example 28 to obtain the target product as a colorless oil.

$^1$H-NMR (CDCl$_3$, 400 MHz): δ 0.94 (3H, t, J=7.3 Hz), 1.26 (3H, s), 1.42 (9H, s), 1.56-1.68 (5H, m), 1.85-1.95 (1H, m), 2.57 (2H, t, J=7.6 Hz), 2.69 (2H, t, J=7.3 Hz), 3.77 (3H, d, J=11.0 Hz), 3.78 (3H, d, J=11.0 Hz), 4.00 (1H, dd, J=9.8, 4.9 Hz), 4.15 (1H, dd, J=9.8, 4.9 Hz), 4.52 (1H, br s), 6.79-6.85 (3H, m), 6.95 (1H, d, J=7.9 Hz), 6.98 (1H, d, J=2.4 Hz), 7.13 (1H, d, J=8.3 Hz), 7.24 (1H, t, J=7.9 Hz).

ESIMS (+): 570 [M+H]$^+$.

Example 36

(R)-2-t-butoxycarbonylamino-5-[2-chloro-4-(3-chlorophenylthio)phenyl]-1-dimethoxyphosphoryloxy-2-methylpentane

[Chemical formula 77]

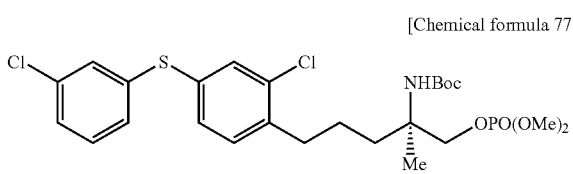

The compound of Example 24 was reacted in the same manner as in Example 28 to obtain the target product as a colorless oil.

$^1$H-NMR (CDCl$_3$, 400 MHz): δ 1.25 (3H, s), 1.42 (9H, s), 1.58-1.67 Hz (3H, m), 1.86-1.96 (1H, m), 2.72 (2H, t, J=6.7 Hz), 3.77 (6H, d, J=11 Hz), 3.98 (1H, dd, J=9.8, 4.9 Hz), 4.15 (1H, dd, J=9.8, 4.9 Hz), 4.52 (1H, br s), 7.15-7.24 (5H, m), 7.36 (1H, d, J=1.8 Hz).

ESIMS (+) 578 [M+H]$^+$.

Example 37

(R)-2-t-butoxycarbonylamino-5-[2-fluoro-4-(3-trifluoromethylphenylthio)phenyl]-1-dimethoxyphosphoryloxy-2-methylpentane

[Chemical formula 78]

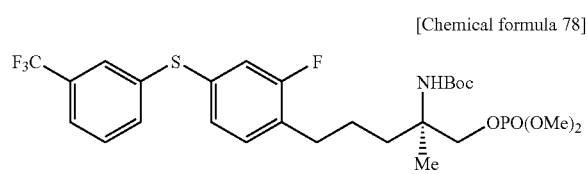

The compound of Example 25 was reacted in the same manner as in Example 28 to obtain the target product as a colorless oil.

$^1$H-NMR (CDCl$_3$, 400 MHz): δ 1.25 (3H, s), 1.42 (9H, s), 1.53-1.68 Hz (3H, m), 1.85-1.97 (1H, m), 2.73 (2H, t, J=6.7 Hz), 3.56 (3H, d, J=11 Hz), 3.57 (3H, d, J=11 Hz), 3.98 (1H, dd, J=9.8, 4.9 Hz), 4.13 (1H, dd, J=9.8, 4.9 Hz), 4.50 (1H, br s), 7.03 (1H, dd, J=9.8 Hz, 1.8 Hz), 7.08 (1H, dd, J=7.9 Hz, 1.8 Hz), 7.16 (1H, t, J=7.9 Hz), 7.38-7.51 (3H, m), 7.55 (1H, br s).

ESIMS (+) 596 [M+H]$^+$.

Example 38

(R)-2-t-butoxycarbonylamino-5-[2-chloro-4-(3-trifluoromethylphenylthio)phenyl]-2-propyl-1-dimethoxyphosphoryloxypentane

[Chemical formula 79]

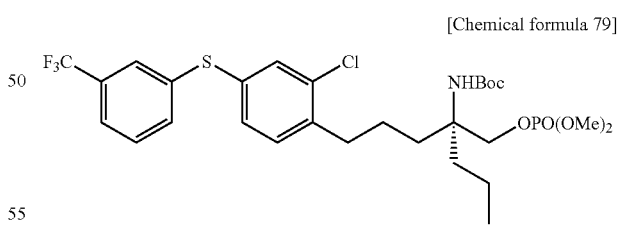

The compound of Example 26 was reacted in the same manner as in Example 28 to obtain the target product as a colorless oil.

$^1$H-NMR (CDCl$_3$, 400 MHz): δ 0.91 (3H, t, J=7.3 Hz), 1.18-1.31 (3H, m), 1.41 (9H, s), 1.48-1.58 (4H, m), 1.75-1.88 (1H, m), 2.71 (2H, t, J=7.3 Hz), 3.76 (6H, d, J=10 Hz), 4.07 (1H, dd, J=9.7, 4.3 Hz), 4.14 (1H, dd, J=9.7, 4.3 Hz), 4.40 (1H, br s), 7.19 (1H, s), 7.20 (1H, d, J=1.8 Hz), 7.38 (1H, d, J=1.8 Hz), 7.41-7.49 (3H, m), 7.55 (1H, br s).

FABMS (+): 640 [M+H]$^+$.

Example 39

(R)-2-t-butoxycarbonylamino-5-[2-chloro-4-(3-difluoromethylphenylthio)phenyl]-1-dimethoxyphosphoryloxy-2-methylpentane

[Chemical formula 80]

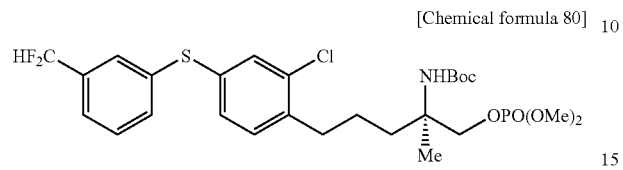

The compound of Example 27 was reacted in the same manner as in Example 28 to obtain the target product as a colorless oil.

$^1$H-NMR (CDCl$_3$, 400 MHz): δ 1.24 (3H, s), 1.42 (9H, s), 1.51-1.67 Hz (3H, m), 1.83-1.99 (1H, m), 2.73 (2H, t, J=7.6 Hz), 3.77 (6H, d, J=11 Hz), 4.00 (1H, dd, J=9.8, 4.9 Hz), 4.17 (1H, dd, J=9.8, 4.9 Hz), 4.54 (1H, br s), 6.61 (1H, t, J=56 Hz), 7.19 (2H, d, J=1.2 Hz), 7.34-7.42 (4H, m), 7.45 (1H, s).

ESIMS (+): 594 [M+H]$^+$.

Example 40

(R)-2-amino-5-[2-chloro-4-(3-trifluoromethylphenoxy)phenyl]-2-methylpentyl phosphoric acid monoester

[Chemical formula 81]

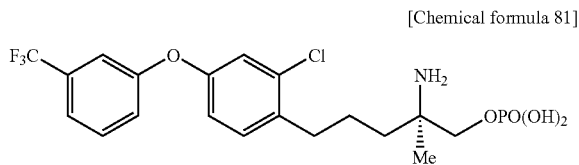

Iodotrimethylsilane (478 μL) was added dropwise under ice cooling and under an argon atmosphere to a solution of the compound of Example 28 (533 mg) in acetonitrile (8 mL), and the resultant solution was stirred under ice cooling for 30 minutes. The solution was charged with water (100 mL), and then further stirred under ice cooling for 30 minutes. The precipitated crystals were then filtered off, thoroughly washed with water and ethyl acetate, and then dried to obtain the target product (310 mg) as a white powder.

$^1$H-NMR (DMSO-d$_6$-dTFA, 400 MHz): δ 1.16 (3H, s), 1.51-1.71 (4H, m), 2.66 (2H, t, J=7.9 Hz), 3.78 (1H, dd, J=11.0, 4.9 Hz), 3.83 (1H, dd, J=11.0, 4.9 Hz), 6.98 (1H, d, J=7.9 Hz), 7.13 (1H, br s), 7.26 (1H, d, J=7.9 Hz), 7.27 (1H, br s), 7.35 (1H, d, J=7.9 Hz), 7.44 (1H, d, J=7.9 Hz), 7.57 (1H, t, J=7.9 Hz).

FABMS (+): 468 [M+H]$^+$.

Elemental Analysis: Measured: C, 48.28%, H, 4.62%, N, 2.86%, Calcd. for C$_{19}$H$_{22}$ClF$_3$NO$_5$P.1/4 H$_2$O: C, 48.32%, H, 4.80%, N, 2.97%.

Optical Rotation: $[α]_D^{25}$+6.62 (c 0.55, DMSO -1% TFA)

Example 41

(R)-2-amino-5-[2-chloro-4-(3-trifluoromethylphenylthio)phenyl]-2-methylpentyl phosphoric acid monoester

[Chemical formula 82]

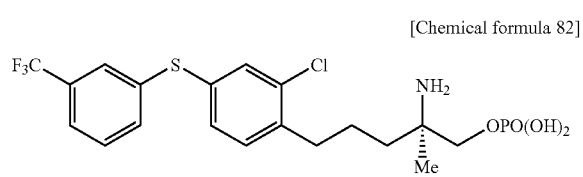

The compound of Example 29 was reacted in the same manner as in Example 40 to obtain the target product as a white powder.

$^1$H-NMR (DMSO-d$_6$-dTFA, 400 MHz): δ 1.15 (3H, s), 1.49-1.68 (4H, m), 2.67 (2H, t, J=7.4 Hz), 3.76 (1H, dd, J=11.0, 4.9 Hz), 3.81 (1H, dd, J=11.0, 4.9 Hz), 7.32 (1H, dd, J=7.9, 2.4 Hz), 7.38 (1H, d, J=7.9 Hz), 7.46 (1H, d,J=2.4 Hz ), 7.53 (1H, d, J=7.9 Hz), 7.56 (1H, d, J=7.9 Hz), 7.60 (1H, br s), 7.62 (1H, t, J=7.9 Hz).

FABMS (+): 484 [M+H]$^+$.

Elemental Analysis: Measured: C 46.85%, H, 4.35%, N, 2.66%, Calcd. for C$_{19}$H$_{22}$ClF$_3$NO$_4$PS: C, 47.16%, H, 4.58%, N, 2.89%

Optical Rotation: $[α]_D^{25}$+7.27 (c0.55, DMSO-1%TFA).

Example 42

(R)-2-amino-4-[2-chloro-4-(3-trifluoromethylphenoxy)phenyl]-2-methylbutyl phosphoric acid monoester

[Chemical formula 83]

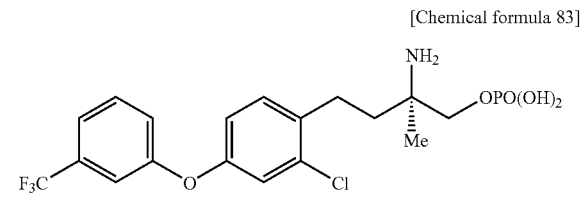

The compound of Example 30 was reacted in the same manner as in Example 40 to obtain the target product as a white powder.

$^1$H-NMR (DMSO-d$_6$-dTFA, 400 MHz): δ 1.30 (3H, s), 1.70-1.90 (2H, m), 2.72 (2H, t, J=8.6 Hz), 3.88 (1H, dd, J=11.0, 5.5 Hz), 3.94 (1H, dd, J=11.0 Hz, 5.5 Hz), 7.04 (1H, dd, J=7.9, 2.4 Hz), 7.20 (1H, d, J=2.4 Hz), 7.30 (1H, dd, J=7.9, 2.4 Hz), 7.34 (1H, br s), 7.39 (1H, d, J=7.9 Hz), 7.51 (1H, d, J=7.9 Hz), 7.62(1H, d, J=7.9 Hz).

FABMS (+): 454 [M+H]$^+$.

Elemental Analysis: Measured: C, 47.83%, H, 4.33%, N, 3.02%, Calcd. for C$_{18}$H$_{20}$ClF$_3$NO$_5$P.1/2 H$_2$O: C, 46.72%, H, 4.57%, N, 3.03%.

Example 43

(R)-2-amino-4-[2-chloro-4-(3-trifluoromethylphenoxy)phenyl]-2-methylbutyl phosphonic acid monoester

[Chemical formula 84]

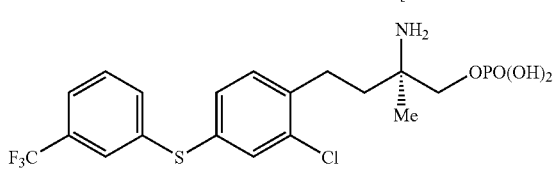

The compound of Example 31 was reacted in the same manner as in Example 40 to obtain the target product as a white powder.

$^1$H-NMR (DMSO-$d_6$-dTFA, 400 MHz): δ 1.28 (3H, s), 1.70-1.90 (2H, m), 2.73 (2H, t, J=8.6 Hz), 3.87 (1H, dd, J=11.0, 4.9 Hz), 3.94 (1H, dd, J=11.0 Hz, 4.9 Hz), 7.33 (1H, d, J=7.9 Hz), 7.39 (1H, d, J=7.9 Hz), 7.46 (1H, br s), 7.50-7.58 (3H, m).

FABMS (+): 470 [M+H]$^+$.

Elemental Analysis: Measured: C, 45.32%, H, 4.09%, N, 2.90%, Calcd. for $C_{18}H_{20}ClF_3NO_4PS.1/4\ H_2O$: C, 45.57%, H, 4.36%, N, 2.95%.

Example 44

(R)-2-amino-4-[2-chloro-4-(3-ethylphenylthio)phenyl]-2-methylbutyl phosphonic acid monoester

[Chemical formula 85]

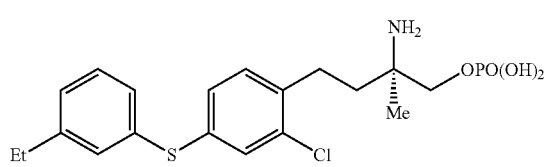

The compound of Example 32 was reacted in the same manner as in Example 40 to obtain the target product as a white powder.

$^1$H-NMR (DMSO-$d_6$-dTFA, 400 MHz): δ 1.37 (3H, t, J=7.3 Hz), 1.28 (3H, s), 1.72-1.85 (2H, m), 2.58 (2H, t, J=7.3 Hz), 2.67-2.72 (2H, m), 3.86 (1H, dd, J=11.0, 4.9 Hz), 3.93 (1H, dd, J=11.0, 4.9 Hz), 7.17-7.21 (3H, m), 7.25-7.26 (2H, m), 7.31 (2H, t, J=7.3 Hz).

ESIMS (+): 430 [M+H]$^+$.

Elemental Analysis Measured: C, 52.56%, H, 5.79%, N, 3.21%, Calcd. For $C_{19}H_{25}ClNO_4PS.1/4H_2O$: C, 52.53%, H, 5.79%, N, 3.21%.

Example 45

(R)-2-amino-5-[2-chloro-4-(3-methylphenoxy)phenyl]-2-methylpentyl phosphonic acid monoester

[Chemical formula 86]

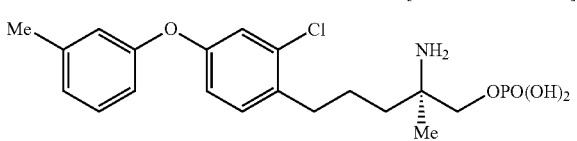

The compound of Example 33 was reacted in the same manner as in Example 40 to obtain the target product as a white powder.

$^1$H-NMR (DMSO-$d_6$-dTFA, 400 MHz): δ 1.17 (3H, s), 1.53-1.71 (4H, m), 2.28 (3H, s), 2.59-2.69 (2H, m), 3.78-3.83 (2H, m), 6.80 (1H, dd, J=7.9, 2.4 Hz), 6.84 (1H, s), 6.92 (1H, dd, J=7.9, 2.4 Hz), 6.98 (1H, d, J=7.9 Hz), 7.02 (1H, d, J=2.4 Hz), 7.27 (1H, t, J=7.9 Hz), 7.33 (1H, d, J=7.9 Hz).

HRESIMS (+): 414.12313 (Calcd. for $C_{19}H_{26}ClNO_5P$ 414.12371).

Elemental Analysis Measured: C, 54.87%, H, 5.89%, N, 3.27%, Calcd. for $C_{19}H_{25}ClNO_5P$: C, 55.14%, H, 6.09%, N, 3.38%.

Optical Rotation: $[\alpha]_D^{25}$+7.93 (c 1.20, DMSO-1% TFA).

Example 46

(R)-2-amino-5-[2-chloro-4-(3-ethylphenylthio)phenyl]-2-methylpentyl phosphonic acid monoester

[Chemical formula 87]

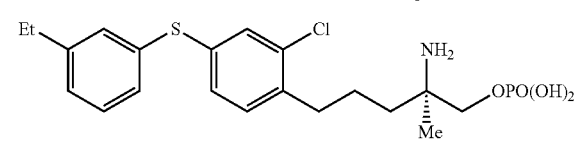

The compound of Example 34 was reacted in the same manner as in Example 40 to obtain the target product as a white powder.

$^1$H-NMR (DMSO-$d_6$-dTFA, 400 MHz): δ 1.41 (3H, t, J=7.3 Hz), 1.16 (3H, s), 1.51-1.69 (4H, m), 2.58 (2H, t, J=7.3 Hz), 2.63-2.80 (2H, m), 3.78 (1H, dd, J=11.0, 4.9 Hz), 3.81 (1H, dd, J=11.0, 4.9 Hz), 7.16-7.33 (7H, m).

ESIMS (+): 444 [M+H]$^+$.

Elemental Analysis Measured: C, 53.87%, H, 6.04%, N, 3.11%, Calcd. for $C_{20}H_{27}ClNO_4PS$: C, 54.11%, H, 6.13%, N, 3.16%.

Example 47

(R)-2-amino-5-[2-chloro-4-(3-propylphenoxy)phenyl]-2-methylpentyl phosphonic acid monoester

[Chemical formula 88]

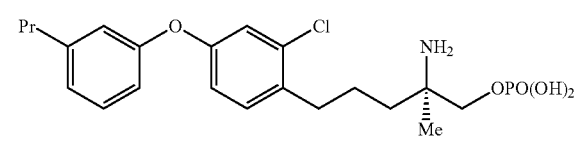

The compound of Example 35 was reacted in the same manner as in Example 40 to obtain the target product as a pale yellow powder.

$^1$H-NMR (DMSO-$d_6$-dTFA, 400 MHz): δ 0.86 (3H, t, J=7.3 Hz), 1.17 (3H, s), 1.51-1.67 (6H, m), 2.53 (2H, t, J=7.3 Hz), 2.64 (2H, t, J=7.3 Hz), 3.78 (1H, dd, J=11.0, 4.9 Hz), 3.83 (1H, dd, J=11.0, 4.9 Hz), 6.81 (1H, dd, J=7.9, 1.8 Hz), 6.86 (1H, t, J=1.8 Hz), 6.91 (1H, dd, J=8.6, 2.4 Hz), 7.00 (1H, d, J=7.9 Hz), 7.02 (1H, d, J=2.4 Hz), 7.29 (1H, t, J=7.9 Hz), 7.33 (1H, t, J=8.6 Hz).

ESIMS (+): 442 [M+H]$^+$.

Example 48

(R)-2-amino-5-[2-chloro-4-(3-chlorophenylthio)phenyl]-2-methylpentyl phosphonic acid monoester

[Chemical formula 89]

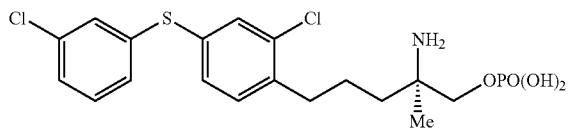

The compound of Example 36 was reacted in the same manner as in Example 40 to obtain the target product as a white powder.

$^1$H-NMR (DMSO-$d_6$-dTFA, 400 MHz): δ 1.17 (3H, s), 1.53-1.71 (4H, m), 2.68 (2H, t, J=6.7 Hz), 3.78 (1H, dd, J=11, 4.9 Hz), 3.83 (1H, dd, J=11, 4.9 Hz), 7.24 (1H, dt, J=7.3, 1.8 Hz), 7.28-7.40 (5H, m), 7.43 (1H, d, J=1.8 Hz).

ESIMS (+): 450 [M+H]$^+$.

Elemental Analysis Measured: C, 47.64%, H, 4.72%, N, 3.07%, Calcd. for $C_{18}H_{22}Cl_2NO_4PS$: C, 48.01%, H, 4.92%, N, 3.11%.

Optical Rotation: $[α]_D^{25}$+8.12 (c 0.55, DMSO-1% TFA).

Example 49

(R)-2-amino-5-[2-fluoro-4-(3-trifluoromethylphenylthio)phenyl]-2-methylpentyl phosphonic acid monoester

[Chemical formula 90]

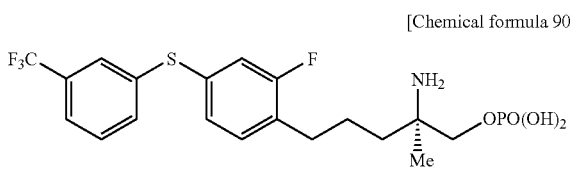

The compound of Example 37 was reacted in the same manner as in Example 40 to obtain the target product as a white powder.

$^1$H-NMR (DMSO-$d_6$-dTFA, 400 MHz): δ 1.16 (3H, s), 1.54-1.66 (4H, m), 2.60 (2H, br s), 3.77 (1H, dd, J=11, 4.9 Hz), 3.82 (1H, dd, J=11, 4.9 Hz), 7.19 (1H, dd, J=7.9, 1.8 Hz), 7.23 (1H, dd, J=9.8, 1.8 Hz), 7.36 (1H, t, J=7.9 Hz), 7.52-7.66 (4H, m).

ESIMS (+): 468 [M+H]$^+$.

Elemental Analysis Measured: C, 48.00%, H, 4.59%, N, 2.88%, Calcd. for $C_{19}H_{22}F_4NO_4PS \cdot 1/2H_2O$: C, 47.90%, H, 4.87%, N, 2.94%.

Elemental Analysis Measured: C, 56.80%, H, 6.40%, N, 3.04%, Calcd. for $C_{21}H_{29}ClNO_5P$: C, 57.08%, H, 6.61%, N, 3.17%.

Optical Rotation: $[α]_D^{25}$+8.33 (c 0.90, DMSO-1% TFA).

Example 50

(R)-2-amino-5-[2-chloro-4-(3-trifluoromethylphenylthio)phenyl]-2-propylpentyl phosphonic acid monoester

[Chemical formula 91]

The compound of Example 38 was reacted in the same manner as in Example 40 to obtain the target product as a white powder.

$^1$H-NMR (DMSO-$d_6$-dTFA, 400 MHz): 0.84 (3H, t, J=7.3 Hz), 1.21 (2H, q, J=7.4 Hz), 1.42-1.62 (6H, m), 2.64-2.71 (2H, m), 3.81 (2H, d, J=4.9 Hz), 7.34 (1H, dd, J=7.9, 1.8 Hz), 7.40 (1H, d, J=7.9 Hz), 7.48 (1H, d, J=1.8 Hz), 7.53 (1H, d, J=7.9 Hz), 7.54-7.66 (3H, m).

FABMS (+): 512 [M+H]$^+$.

Elemental Analysis Measured: C, 47.89%, H, 4.94%, N, 2.65, Calcd. for $C_{21}H_{26}ClF_3NO_4PS \cdot H_2O$: C, 47.65%, H, 5.33%, N, 2.65%.

Example 51

(R)-2-amino-5-[2-chloro-4-(3-difluoromethylphenylthio)phenyl]-2-methylpentyl phosphonic acid monoester

[Chemical formula 92]

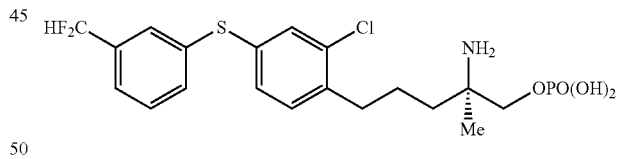

The compound of Example 39 was reacted in the same manner as in Example 40 to obtain the target product as a white powder.

$^1$H-NMR (DMSO-$d_6$-dTFA, 400 MHz): δ 1.16 (3H, s), 1.50-1.71 (4H, m), 2.62-2.73 (2H, m), 3.78 (1H, dd, J=11.0, 4.9 Hz), 3.83 (1H, dd, J=11.0, 4.9 Hz), 6.98 (1H, dd, J=56, 1.8 Hz), 7.27 (1H, dd, J=7.9, 1.8 Hz), 7.37 (1H, d, J=7.9 Hz), 7.39 (1H, d, J=1.8 Hz), 7.43-7.56 (4H, m).

ESIMS (+): 466 [M+H]$^+$.

Elemental Analysis Measured: C, 48.51%, H, 4.79%, N, 2.93%, Calcd. for $C_{19}H_{23}ClF_2NO_4PS \cdot 1/5H_2O$: C, 48.51%, H, 5.02%, N, 2.98%.

Optical Rotation: $[α]_D^{25}$+5.32 (c0.50, DMSO-1% TFA).

Example 52

Diethyl 2-{3-[2-chloro-4-(3-trifluoromethylphenylthio)phenyl]propyl-2-methylmalonate

[Chemical formula 93]

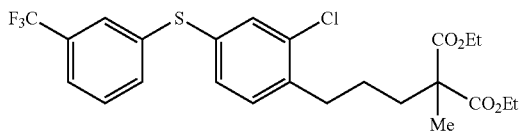

2-Chloro-1-(3-iodopropyl)-4-(3-trifluoromethylphenylthio)benzene and diethyl 2-methylmalonate were reacted according to the same procedures as in Example 152 of WO 04026817 to obtain the target product as a colorless oil.

$^1$H-NMR (CDCl$_3$, 400 MHz): δ 1.25 (6H, t, J=7.4 Hz), 1.40 (3H, s), 1.51-1.63 (2H, m), 1.90-1.97 (2H, m), 2.73 (2H, t, J=7.9 Hz), 4.17 (4H, q, J=7.4 Hz), 7.17-7.23 (2H, m), 7.38 (1H, d, J=2.2 Hz), 7.39-7.44 (2H, m), 7.45-7.50 (1H, m), 7.55 (1H, s).

EIMS (+): 502 [M]$^+$.

Example 53

(±)-5-[2-chloro-4-(3-trifluoromethylphenylthio)phenyl]-2-ethoxylcarbonyl-2-methylpentanoic acid

[Chemical formula 94]

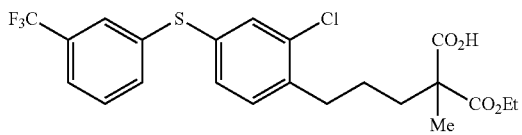

To a solution of the compound of Example 52 (16.8 g) in ethanol (167 mL) was added potassium hydroxide (2.40 g), and the resultant solution was stirred at 50° C. for 24 hours. To the reaction solution was added water, neutralized with 2 mol/L hydrochloric acid, and extracted with ethyl acetate. The organic layer was washed with water and saturated brine in that order, and then dried over anhydrous sodium sulfate. The solvent was evaporated, and the resultant residue was purified by silica gel column chromatography (hexane:ethyl acetate=1:1) to obtain the target product (11.2 g) as a colorless oil.

$^1$H-NMR (CDCl$_3$, 400 MHz): δ 1.26 (3H, t, J=7.4 Hz), 1.47 (3H, s), 1.55-1.66 (2H, m), 1.87-2.06 (2H, m), 2.73 (2H, t, J=7.9 Hz), 4.22 (2H, q, J=7.4 Hz), 7.18 (1H, d, J=7.9 Hz), 7.20 (1H, dd, J=7.9, 1.8 Hz), 7.38 (1H, d, J=1.8 Hz), 7.39-7.44 (2H, m), 7.45-7.50 (1H, m), 7.54 (1H, s).

ESIMS (+): 475 [M+H]$^+$.

Example 54

Ethyl (±)-5-[2-chloro-4-(3-trifluoromethylphenylthio)phenyl]-2-methoxycarbonylamino-2-methylpentanoate

[Chemical formula 95]

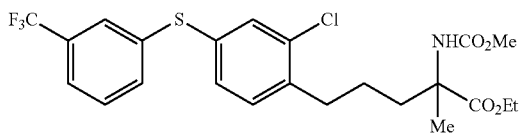

To a solution of the compound of Example 53 (15.8 g) in benzene (166 mL) was added diphenylphosphoryl azide (7.86 mL) and triethylamine (6.01 mL), and the resultant solution was heated to reflux for 1.5 hours. The temperature of the reaction solution was returned to room temperature, and methanol (20 mL) was added dropwise thereto over 20 minutes. The resultant solution was heated to reflux for 30 minutes, and then sodium methoxide (3.58 g) was added to the reaction mixture. The resultant solution was heated to reflux for 1.5 hours. To the reaction solution was added saturated aqueous ammonium chloride, and extracted with ethyl acetate. The organic layer was washed with water and saturated brine in that order, and then dried over anhydrous sodium sulfate. The solvent was evaporated, and the resultant residue was purified by silica gel column chromatography (hexane:ethyl acetate=5:1) to obtain the target product (15.6 g) as a colorless oil.

$^1$H-NMR (CDCl$_3$, 400 MHz): δ 1.25 (3H, t, J=7.3 Hz), 1.32-1.47 (1H, m), 1.52-1.67 (1H, m), 1.57 (3H, s), 1.80-1.90 (1H, m), 2.20-2.37 (1H, m), 2.62-2.76 (2H, m), 3.64 (3H, s), 4.15-4.25 (2H, m), 5.62 (1H, br s), 7.16 (1H, d, J=7.9 Hz), 7.20 (1H, dd, J=7.9, 1.8 Hz), 7.38 (1H, d, J=1.8 Hz), 7.40-7.44 (2H, m), 7.45-7.50 (1H, m), 7.55 (1H, s).

ESIMS (+): 504 [M+H]$^+$.

Example 55

(±)-5-[2-chloro-4-(3-trifluoromethylphenylthio)phenyl]-2-methoxycarbonylamino-2-methylpentan-1-ol

[Chemical formula 96]

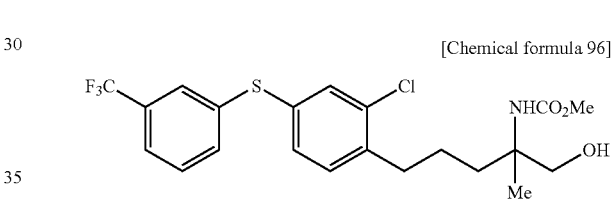

To a solution of the compound of Example 54 (15.6 g) in THF (249 mL) was added under ice cooling lithium borohydride (3.75 g), and then ethanol (16.6 mL) was added dropwise. The resultant solution was then stirred for 1 hour under ice cooling. To the reaction solution was added 10% aqueous citric acid, extracted with ethyl acetate, washed with water and saturated brine in that order, and then dried over anhydrous sodium sulfate. The solvent was evaporated, and the resultant residue was purified by silica gel column chromatography (hexane:ethyl acetate=1:1) to obtain the target product (12.9 g) as a colorless oil.

$^1$H-NMR (CDCl$_3$, 400 MHz): δ 1.18 (3H, s), 1.54-1.74 (3H, m), 1.78-1.89 (1H, m), 2.73 (2H, t, J=7.9 Hz), 3.63 (3H, s), 3.56-3.70 (2H, m), 4.23 (1H, br s), 7.17-7.22 (2H, m), 7.38-7.50 (4H, m), 7.54 (1H, s).

ESIMS (+): 462 [M+H]$^+$.

Example 56

(±)-2-t-butoxycarbonylamino-5-[2-chloro-4-(3-trifluoromethylphenylthio)phenyl]-2-methylpentan-1-ol

[Chemical formula 97]

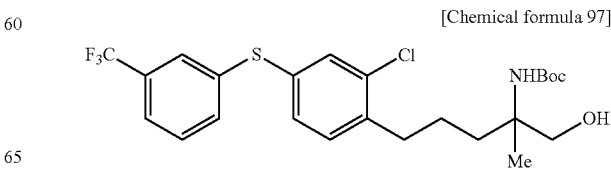

To a solution of the compound of Example 55 (12.9 g) in THF (60 mL) and methanol (120 mL) was added under ice cooling 5 mol/L aqueous potassium hydroxide solution (60 mL), and the resultant solution was heated to reflux for 86 hours. To the reaction solution was added water, extracted with ethyl acetate, washed with water and saturated brine in that order, and then dried over anhydrous sodium sulfate. The extract was concentrated, the residue was dissolved in 1,4-dioxane (279 mL), and the resultant solution was charged with di-tert-butoxydicarbonate (9.13 g). The solution was stirred at room temperature for 2 hours and then left to stand at room temperature overnight. To the reaction solution was added water, extracted with ethyl acetate, washed with water and saturated brine in that order, and then dried over anhydrous sodium sulfate. The solvent was evaporated, and the resultant residue was purified by silica gel column chromatography (hexane:ethyl acetate=2:1) to obtain the target product (13.0 g) as a colorless oil.

$^1$H-NMR (CDCl$_3$, 400 MHz): δ 1.14 (3H, s), 1.42 (9H, s), 1.53-1.74 (3H, m), 1.79-1.92 (1H, m), 2.74 (2H, t, J=7.9 Hz), 3.58-3.69 (2H, m), 4.05 (1H, br s), 4.57 (1H, br s), 7.20-7.22 (2H, m), 7.38-7.50 (4H, m), 7.54 (1H, s).

ESIMS (+): 504 [M+H]$^+$.

Examples 57 and 58

(+)-2-t-butoxycarbonylamino-5-[2-chloro-4-(3-trifluoromethylphenylthio)phenyl]-2-methylpentan-1-ol and (−)-2-t-butoxycarbonylamino-5-[2-chloro-4-(3-trifluoromethylphenylthio)phenyl]-2-methylpentan-1-ol The compound of Example 56 was subjected to optical resolution using high performance liquid chromatography (CHIRALCEL OJ-H, hexane:isopropanol:diethylamine=98:2:0.1 (v/v), measurement wavelength: UV 278 nm, flow rate: 1.0 mL/min). From the pre-elution portion, a colorless oil having $[\alpha]_D^{25}$+15.08 (c 0.63, CHCl$_3$) was obtained (Example 57), and from the post-elution portion, a colorless oil with $[\alpha]_D^{26}$-13.91 (c 0.63, CHCl$_3$) was obtained (Example 58).

Example 59

(+)-2-amino-5-[2-chloro-4-(3-trifluoromethylphenoxy)phenyl]-2-methylpentylphosphonic acid monoester The compound of Example 57 was reacted in the same manner as in Example 16, and the resultant compound was then reacted in the same manner as in Example 28 to obtain a phosphate, which was then reacted in the same manner as in Example 40 to obtain the target product as a white powder.

FABMS (+): 484 [M+H]$^+$

Optical Rotation: $[\alpha]_D^{25}$+8.86 (c 1.00, DMSO-1% TFA)

Next, results which support the utility of the compound of the present invention will be shown by an experiment example.

Experiment Example 1

Intracellular Calcium Mobilization Induced Test of a Subject Compound Against Human S1P (sphingosine-1-phosphate) Receptor-expressing Cells Human S1P receptors expressing CHO-K1 cells (hS1P$_1$ receptors expressing CHO-K1 cells, hS1P$_3$ receptors expressing CHO-K1 cells, and hS1P$_4$ receptors expressing CHO-K1 cells), were maintained in Ham's F-12 medium containing 10% fetal bovine serum and 400 μg/mL Geneticin. Into a black, clear bottom, culture plate (BD Falcon) with 96 wells, 7×10$^4$ cells/well of the hS1P$_1$ and hS1P$_3$ receptors expressing CHO-K1 cells were plated, and ×10$^4$ cells/well of the hS1P$_4$ receptors expressing CHO-K1 cells were plated. The cells were incubated overnight at 37° C. at 5% CO$_2$. The medium in the wells were removed by suction. A loading buffer included in a Calcium Kit-Fluo 3 reagent (Dojindo Laboratories) was added as a fluorescent Ca$^{2+}$-binding indicator. The cells were incubated for 80 minutes at 37° C. at 5% CO$_2$. After the incubation, the wells were washed with PBS. A recording buffer included in a Calcium Kit-Fluo 3 reagent was added, and the cells were incubated for 20 minutes at 37° C. at 5% CO$_2$. Using a microplate spectrophotofluorometer (FLEX Station, Molecular Devices), the fluorescence intensity at an excitation wavelength of 485 nm and a detection wavelength of 525 nm was measured. S1P and the subject compound prepared in medium so that the concentration was 10-fold that of the final concentration (final DMSO concentration of 0.1%). The solution was added 18 seconds after the fluorescence measurement was started, and then fluorescence intensity was continuously measured every 1.5 seconds until 100 seconds after addition. A value (fluorescence increase) obtained by subtracting the minimum fluorescence intensity from the maximum fluorescence intensity was calculated from the measurement data. Taking the difference between the fluorescence increase when the solvent was added and the fluorescence increase when the S1P was allowed to act at 10$^{-6}$ M as 100%, the fluorescence increase ratio (%) of the subject compound was calculated. Taking this value as the intracellular calcium mobilization induced activity of the subject compound, the EC$_{50}$ value was determined using PRISM software (GraphPad). In Table 1, 10 nmol/L>EC$_{50}$ value ≧1 nmol/L is indicated as a +, and 1 nmol/L>EC$_{50}$ value is indicated as a ++.

TABLE 1

| Example No. | S1P1 | S1P3 | S1P4 |
|---|---|---|---|
| 40 | ++ | >10 μmol/L | + |
| 41 | ++ | >10 μmol/L | + |
| 42 | ++ | >10 μmol/L | + |
| 43 | ++ | >10 μmol/L | + |
| 44 | ++ | >10 μmol/L | + |
| 45 | ++ | >10 μmol/L | + |
| 46 | ++ | >10 μmol/L | + |
| 47 | ++ | >10 μmol/L | + |
| 48 | + | >10 μmol/L | ++ |
| 49 | ++ | >10 μmol/L | + |
| 50 | ++ | >10 μmol/L | + |
| 51 | + | >10 μmol/L | + |

From the above results, it was determined that the compound of the present invention has a weak activity on a human S1P$_3$ receptor, and a strong activity on S1P$_1$ and S1P$_4$ receptors.

INDUSTRIAL APPLICABILITY

The present invention has led to the discovery of a novel amino phosphate derivative and addition salt thereof, which have an excellent S1P receptor modulatory action. A compound having such an S1P receptor modulatory action is effective as a treatment and a preventive agent for arteriosclerosis, arteriosclerosis obliterans, thromboangiitis obliterans, renal fibrosis, hepatic fibrosis, chronic bronchial asthma, diffuse pulmonary hamartoangiomyomatosis, adult respiratory distress syndrome (ARDS), chronic obstructive pulmonary disease (COPD), pneumonitis, idiopathic interstitial pneumonia, lung cancer, pneumonia hypersensitivity, Buerger's disease, diabetic neuropathy peripheral arterial disease, septicemia, angiitis, nephritis, pneumonia, cerebral infarction, myocardial infarction, edematous state, varices, dissecting aortic aneurysm, angina pectoris, DIC, pleurisy, congestive heart failure, multiple organ failure, bedsores, burns, ulcerative colitis, Crohn's disease and the like. Furthermore, a compound having such an S1P receptor modulatory action is effective as a treatment and a preventive agent for rejection of heart transplants, kidney transplants, skin grafts, liver transplants, and bone marrow transplants, and is also an effective as a treatment and a preventive agent for rheumatoid arthritis, lupus nephritis, systemic lupus erythematosus, Hashimoto's disease, multiple sclerosis, myasthenia gravis, diabetes mellitus, atopic dermatitis, allergic rhinitis, allergic conjunctivitis, allergic contact dermatitis and the like.

The invention claimed is:

1. An amino phosphate derivative represented by the general formula (1a),

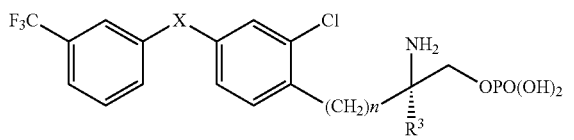

(1a)

wherein $R^3$ represents a straight-chain alkyl group having 1 to 3 carbon atoms, X represents an oxygen atom or a sulfur atom, and n denotes 2 or 3, or a pharmaceutically acceptable salt or hydrate thereof.

2. The amino phosphate derivative according to claim 1, wherein the compound represented by the general formula (1a) is,
(R)-2-amino-5-[2-chloro-4-(3-trifluoromethylphenoxy)phenyl]-2-methylpentyl phosphoric acid monoester,
(R)-2-amino-5-[2-chloro-4-(3-trifluoromethylphenylthio)phenyl]-2-methylpentyl phosphoric acid monoester,
(R)-2-amino-4-[2-chloro-4-(3-trifluoromethylphenoxy)phenyl]-2-methylbutyl phosphoric acid monoester,
(R)-2-amino-4-[2-chloro-4-(3-trifluoromethylphenylthio)phenyl]-2-methylbutyl phosphoric acid monoester,
(R)-2-amino-5-[2-chloro-4-(3-trifluoromethylphenylthio)phenyl]-2-propylpentyl phosphoric acid monoester, or a pharmaceutically acceptable salt or hydrate thereof.

3. An amino phosphate derivative represented by the general formula (1),

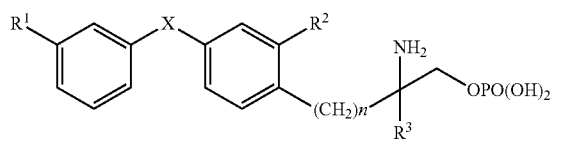

(1)

wherein $R^1$ represents a trifluoromethyl group, $R^2$ represents a chlorine atom, $R^3$ represents a straight-chain alkyl group having 1 to 3 carbon atoms, X represents an oxygen atom or a sulfur atom, and n denotes 2 or 3, obtainable by a step of allowing a compound represented by the general formula (2),

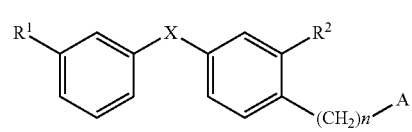

(2)

wherein $R^1$ represents a trifluoromethyl group, $R^2$ represents a chlorine atom, A represents a halogen atom, X represents an oxygen atom or a sulfur atom, and n denotes 2 or 3, and a compound represented by the general formula (12),

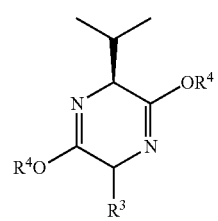

(12)

wherein $R^3$ represents a straight-chain alkyl group having 1 to 3 carbon atoms and $R^4$ represents an alkyl group having 1 to 6 carbon atoms, to react in the presence of a base,
a step of subjecting the resultant product to acid decomposition, protecting a nitrogen atom with a t-butoxycarbonyl group, and then reducing the product,
a step of reacting the reduction product with a compound represented by the general formula (10), $$P(OR^6)_3 \qquad (10)$$

wherein $R^6$ represents an alkyl group having 1 to 6 carbon atoms or a benzyl group,
and a step of subjecting the resultant product obtained by the previous steps to acid decomposition or a halogenosilane treatment,
or a pharmaceutically acceptable salt or hydrate thereof.

4. The amino phosphate derivative according to claim 1, wherein in the general formula (1a), $R^3$ is a methyl group, or a pharmaceutically acceptable salt or hydrate thereof.

5. An S1P receptor modulator comprising the amino phosphate derivative, or a pharmaceutically acceptable salt or hydrate thereof, according to claim 1 as an active ingredient.

6. An S1P receptor modulator comprising the amino phosphate derivative, or a pharmaceutically acceptable salt or hydrate thereof, according to claim 2 as an active ingredient.

7. An S1P receptor modulator comprising the amino phosphate derivative, or a pharmaceutically acceptable salt or hydrate thereof, according to claim 3 as an active ingredient.

8. An S1P receptor modulator comprising the amino phosphate derivative, or a pharmaceutically acceptable salt or hydrate thereof, according to claim 4 as an active ingredient.

9. A pharmaceutical comprising the amino phosphate derivative, or a pharmaceutically acceptable salt or hydrate thereof, according to claim 1 as an active ingredient.

10. A pharmaceutical comprising the amino phosphate derivative, or a pharmaceutically acceptable salt or hydrate thereof, according to claim 2 as an active ingredient.

11. A pharmaceutical comprising the amino phosphate derivative, or a pharmaceutically acceptable salt or hydrate thereof, according to claim 3 as an active ingredient.

12. A pharmaceutical comprising the amino phosphate derivative, or a pharmaceutically acceptable salt or hydrate thereof, according to claim 4 as an active ingredient.

13. An amino phosphate derivative represented by (+)-2-amino-5-[2-chloro-4-(3-trifluoromethylphenoxy)phenyl]-2-methylpentyl phosphoric acid monoester, (+)-2-amino-5-[2-chloro-4-(3-trifluoromethylphenylthio)phenyl]-2-methylpentyl phosphoric acid monoester, or a pharmaceutically acceptable salt or hydrate thereof.

14. An S1P receptor modulator comprising the amino phosphate derivative, or a pharmaceutically acceptable salt or hydrate thereof, according to claim 13 as an active ingredient.

15. A pharmaceutical comprising the amino phosphate derivative, or a pharmaceutically acceptable salt or hydrate thereof, according to claim 13 as an active ingredient.

16. The amino phosphate derivative according to claim 1, wherein the compound represented by the general formula (1a) is the compound represented by the formulae (1b), (1c), (1d), (1e), or (1f):

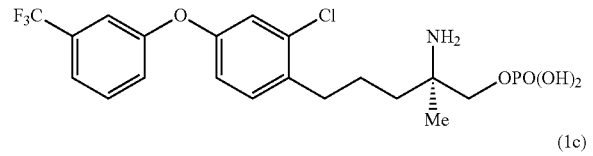
(1b)

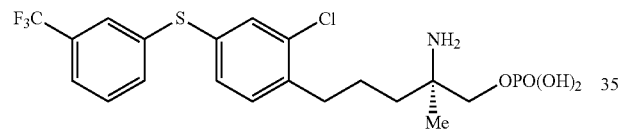
(1c)

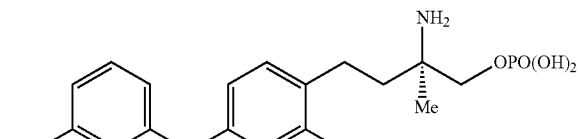
(1d)

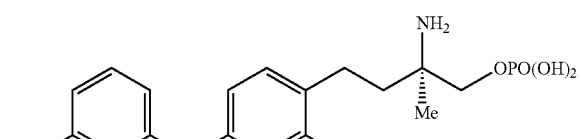
(1e)

(1f)

or a pharmaceutically acceptable salt or hydrate thereof.

17. An S1P receptor modulator comprising the amino phosphate derivative, or a pharmaceutically acceptable salt or hydrate thereof, according to claim 16 as an active ingredient.

18. A pharmaceutical comprising the amino phosphate derivative, or a pharmaceutically acceptable salt or hydrate thereof, according to claim 16 as an active ingredient.

* * * * *